(12) United States Patent
Schulze et al.

(10) Patent No.: US 7,700,311 B2
(45) Date of Patent: Apr. 20, 2010

(54) ALCOHOL DEHYDROGENASES

(75) Inventors: Renate Schulze, Bensheim (DE);
Patrick Lorenz, Lorsch (DE); Jürgen Eck, Bensheim (DE); Oliver May, Frankfurt (DE); Harald Gröger, Hanau (DE); Harald Trauthwein, Frankfurt (DE)

(73) Assignee: Degussa AG, Dusseldorf (DE)

( * ) Notice: Subject to any disclaimer, the term of this patent is extended or adjusted under 35 U.S.C. 154(b) by 614 days.

(21) Appl. No.: 10/593,119

(22) PCT Filed: Mar. 10, 2005

(86) PCT No.: PCT/EP2005/002557

§ 371 (c)(1),
(2), (4) Date: Sep. 18, 2006

(87) PCT Pub. No.: WO2005/103239

PCT Pub. Date: Nov. 3, 2005

(65) Prior Publication Data

US 2008/0216181 A1 Sep. 4, 2008

(30) Foreign Application Priority Data

Mar. 22, 2004 (DE) .................. 10 2004 014 274

(51) Int. Cl.
*C12Q 1/26* (2006.01)
*C12N 9/02* (2006.01)

(52) U.S. Cl. .......................... 435/25; 435/189
(58) Field of Classification Search .................. 435/25, 435/189
See application file for complete search history.

(56) References Cited

U.S. PATENT DOCUMENTS

| 6,781,009 | B2 | 8/2004 | Wakita |
| 6,884,607 | B2 | 4/2005 | Asako et al. |
| 2003/0105347 | A1 | 6/2003 | Wakita et al. |
| 2003/0134402 | A1 | 7/2003 | Asako et al. |
| 2005/0272136 | A1 | 12/2005 | Itoh et al. |
| 2006/0246561 | A1 | 11/2006 | Hummel et al. |

FOREIGN PATENT DOCUMENTS

| DE | 42 09 022 A1 | 10/1993 |
| EP | 1382683 A2 | 1/2003 |

OTHER PUBLICATIONS

Wang, et al., "Cloning sequence analysis and expression in *Escherichia coli* of the gene encoding phenylacetaldehydereductase from styrene-assimilating Corynebacterium sp. strain ST-10," *Appl. Microbiol. Biotechnol*. 52:386-392 (1999).
Hummel, W., "New alcohol dehydrogenases for the synthesis of chiral compounds," *Adv. Biochem. Eng. Biotechnol*. 58:145-184 (1997).
International Search Report dated Sep. 3, 2003 for PCT/EP03/03375.
European Search Report dated Sep. 13, 2007 for EP 07 10 8047.
English Abstract for DE 42 09 022 A1 cited as B1 above, (1993).
Database EMBL Online, Accession Nos. Q9ZN85 and AB020760, (1995).
Hummel, et al., "Chiral Alcohols by Enantioselective Enzymatic Oxidation," *Annals New York Academy of Sciences* 799:713-716 (1996).
Itoh, et al., "Purification and Characterization of Phenylacetaldehyde Reductase from a Styrene-Assimilating *Corynebacterium* Strain, ST-10," *Appl. Environ. Microbiol*. 63(10): 3783-3788 (Oct. 1997).
Itoh, et al., "Production of Chiral Alcohols by Enantioselective Reduction with NADH-Dependent Phenylacetaldehyde Reductase from *Corynebacterium* Strain, ST-10,"*J. Mol. Catalysis B: Enzymatic* 6:41-50 (1999).
Reid, et al., "Molecular Characterization of Microbial Alcohol Dehydrogenases," *Critical Reviews in Microbiology* 20(1):13-56 (1994).
Schenkels, et al., "Nicotinoprotein (NADH-Containing) Alcohol Dehydrogenase from *Rhodococcus erythropolis* DSM 1069: An Efficient Catalyst for Coenzyme-Independent Oxidation of a Broad Spectrum of Alcohols and the Interconversion of Alcohols and Aldehydes," *Microbiol*. 146:775-785 (2000).
Written Opinion of the International Searching Authority for PCT/EP2005/002557 filed Mar. 10, 2005.
International Preliminary Report on Patentability for PCT/EP2005/002557 filed Mar. 10, 2005.

*Primary Examiner*—Tekchand Saidha
(74) *Attorney, Agent, or Firm*—Law Office of Michael A. Sanzo, LLC

(57) ABSTRACT

The invention relates to novel polypeptides which have the biological activity of an NAD- or NADP-dependent alcohol dehydrogenase. The invention furthermore relates to nucleic acids encoding said polypeptides, to nonhuman hosts or host cells and to reaction systems which may be used for preparing desired products. The polypeptides of the invention are preferably used in the preparation, starting from aldehydes or ketones, of primary and enantiomerically pure secondary alcohols which may serve as intermediates for medicaments. Alternatively, the polypeptides of the invention may also be employed in the reverse reaction, i.e. the oxidation of alcohols with the formation of aldehydes or ketones.

20 Claims, 3 Drawing Sheets

Figure 2:
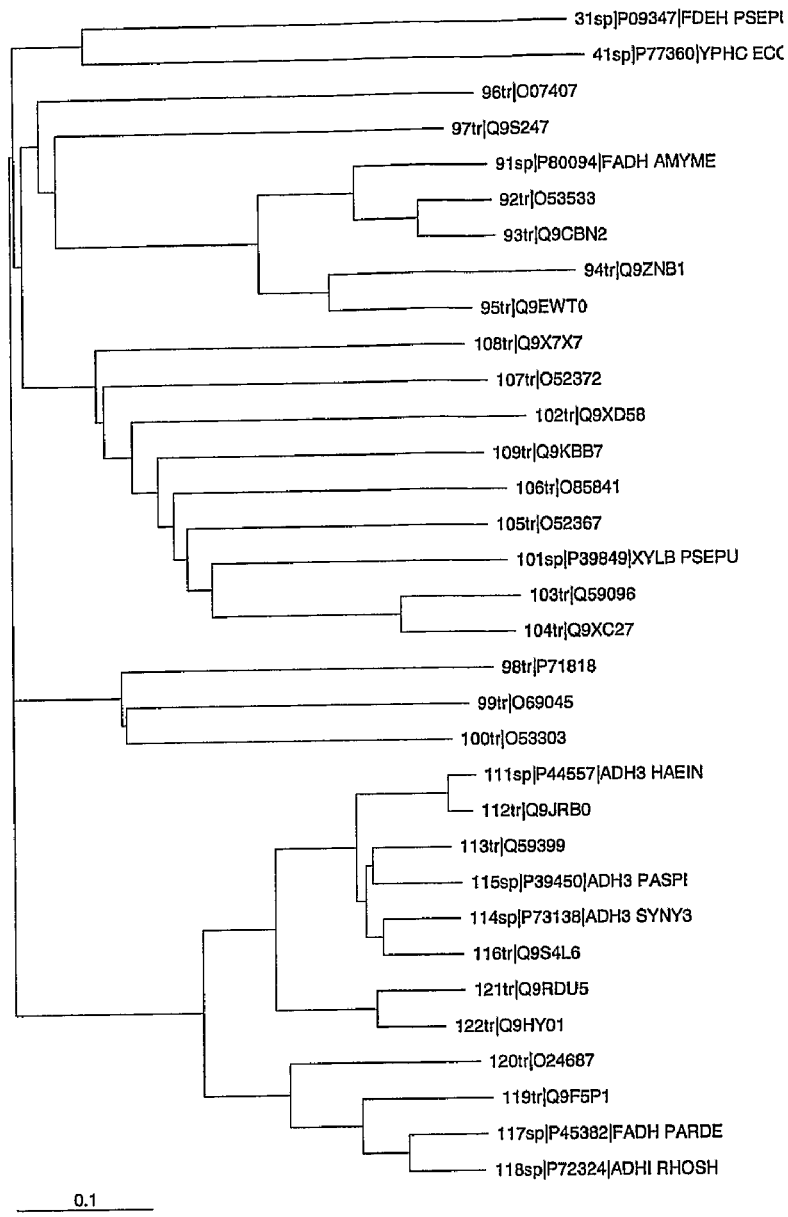

- Prior art via resolution of the racemate: at least 3-4 steps
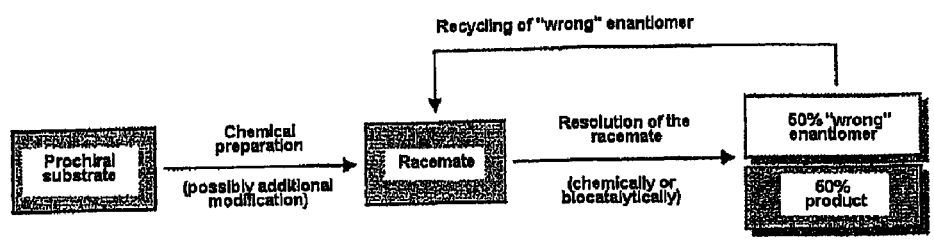
Fig. (1a)
- Biocatalytic and sustainable concept: Asymmetrical biocatalysis
Fig. (1b)

Overview of cluster 2 (= primer group 2), based on 33 sequences

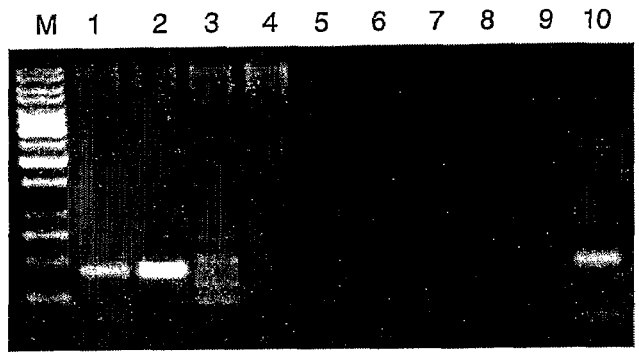

Fig. 3

PCR typing with primer group 2, using various pools

Lane occupation: M: Marker 1 kb DNA ladder; Lane 1: Pool 1 with primers ADHM9 + 10; Lane 2: Pool 1 with primers ADHM11 + 12; Lane 3: Pool 1 with primers ADHM13 + 14; Lane 4: Pool 1 with primers ADHM15 + 16; Lane 5: Pool 2 with primers ADHM 9 + 10; Lane 6: Pool 2 with primers ADHM11 + 12; Lane 7: Pool 2 with primers ADHM13 + 14; Lane 8: Pool 2 with primers ADHM15 + 16; Lane 9: Pool 3 with primers ADHM9 + 10; Lane 10: Pool 3 with primers ADHM11 + 12

ALCOHOL DEHYDROGENASES

CROSS REFERENCE TO RELATED APPLICATIONS

The present application represents U.S. national stage of international application PCT/EP2005/002557, which had an international filing date of Mar. 10, 2005 and which was published in English under PCT Article 21(2) on Nov. 3, 2005. The international application claims priority to German application 10 2004 014 274.2, filed on Mar. 22, 2004.

The invention relates to novel polypeptides which have the biological activity of an NAD- or NADP-dependent alcohol dehydrogenase. The invention furthermore relates to nucleic acids encoding said polypeptides, to nonhuman hosts or host cells and to reaction systems which may be used for preparing desired products. The polypeptides of the invention are preferably used in the preparation, starting from aldehydes or ketones, of primary and enantiomerically pure secondary alcohols which may serve as intermediates for medicaments. Alternatively, the polypeptides of the invention may also be employed in the reverse reaction, i.e. the oxidation of alcohols with the formation of aldehydes or ketones.

The description makes reference to a number of documents. The disclosure content of these documents is hereby incorporated by reference.

Enantiomerically pure alcohols are among the most important chiral building blocks of industrial special and fine chemistry. These products act, inter alia, as essential key intermediates in the preparation of medicaments. For a long time, the industrial route to these target molecules went preferably via purely chemical processes, for example by way of resolution of the racemate. This involves, starting from a ketone, firstly preparing the alcohol in its racemic form and then isolating the desired enantiomer in a resolution of the racemate with the aid of at least stoichiometric amounts of a chiral auxiliary substance. Disadvantages of these methods include not only the 50% maximum yield of the resolution of the racemate but must also be seen in the use of numerous ecologically problematic starting compounds for preparing the racemate. Further disadvantages are the additional step of recycling the undesired enantiomer as well as the need of chiral auxiliary reagents (moreover, stoichiometric amounts thereof) for the resolution of the racemate. The concept of the resolution of the racemate is summarized in the equation (1a) in the overview in FIG. 1. A first substantial progress toward a more sustainable process was achieved using the biocatalytic resolution of the racemate, thereby dispensing with the necessity of employing stoichiometric amounts of chiral auxiliary reagents. Regrettably, however, all other disadvantages listed above remained relevant, despite such a biocatalytic route.

One possible way of avoiding the above-described disadvantages of the resolution of the racemate or of diastereoselective syntheses is the direct conversion of ketones to the desired optically active alcohols in one step. Such "direct asymmetrical processes" may be carried out firstly by using metal-containing chemocatalysts, with the chemocatalysts employed being heavy metal-containing complexes which include a chiral ligand. Besides the use of ecologically problematic heavy metals as a substantial catalyst component, the need for expensive and partly very sensitive ligands, for example phosphane ligands, is also disadvantageous.

Another alternative is the direct asymmetrical reduction using suitable biocatalysts for quantitative conversion of prochiral substrates to the desired enantiomerically pure product. Here too, the number of reaction steps is reduced to the theoretically possible minimum of only one step, the biocatalytic conversion is carried out under ecologically excellent conditions (inter alia water as a solvent), and the process as such proceeds with high atom economy. The concept of a biocatalytic and sustainable process of this kind is set out in the equation (1b) of the overview in FIG. 1.

One disadvantage of the biocatalytic variant, however, is the lack of alcohol dehydrogenases available on an industrial scale as suitable biocatalysts for the target reaction and expression thereof. The object on which the present invention is based was therefore to obtain novel, efficient and industrially usable alcohol dehydrogenases. This object is achieved by the embodiments characterized in the claims.

Thus, the invention relates to a polypeptide which has the biological activity of an NAD- or NADP-dependent alcohol dehydrogenase and which comprises or has one of the following sequences: the sequence of SEQ ID NO.: 1, the sequence of SEQ ID NO.: 2, the sequence of SEQ ID NO.: 3 or a sequence which is at least 90% identical to the sequence of SEQ ID NO.: 3. Said sequence is preferably at least 95% identical to SEQ ID NO.: 3. More preferably, said sequence is at least 98% or 99% identical to SEQ ID NO.: 3. Also comprised is the sequence of SEQ ID NO.: 4. Furthermore comprised is the sequence of SEQ ID NO.: 5 or a sequence which is at least 90% identical to the sequence of SEQ ID NO.: 5. Preferably, said sequence is at least 95% identical to SEQ ID NO.: 5. More preferably, said sequence is at least 98% or 99% identical to SEQ ID NO.:5. Also comprised is the sequence of SEQ ID NO.: 6 or a sequence which is at least 90% identical to the sequence of SEQ ID NO.: 6. Preferably, said sequence is at least 95% identical to SEQ ID NO.: 6. More preferably, said sequence is at least 98% or 99% identical to SEQ ID NO.: 6. Likewise comprised is the sequence of SEQ ID NO.: 7 or a sequence which is at least 70% identical to the sequence of SEQ ID NO.: 7. Preferably, said sequence is at least 75% identical to SEQ ID NO.: 7. More preferably, said sequence is at least 80% identical to the sequence of SEQ ID NO.: 7. Even more preferably, said sequence is at least 85%, 90%, 95%, 98% or 99% identical to the sequence of SEQ ID NO.: 7. Also comprised is the sequence of SEQ ID NO.: 8 or a sequence which is at least 70% identical to the sequence of SEQ ID NO.: 8. Preferably, said sequence is at least 75% identical to SEQ ID NO.: 8. More preferably, said sequence is at least 80% identical to the sequence of SEQ ID NO.: 8. Even more preferably, said sequence is at least 85%, 90%, 95%, 98% or 99% identical to the sequence of SEQ ID NO.: 8.

Additionally comprised is the sequence of SEQ ID NO.: 9 or a sequence which is at least 70% identical to the sequence of SEQ ID NO.: 9. Preferably, said sequence is at least 75% identical to SEQ ID NO.: 9. More preferably, said sequence is at least 80% identical to the sequence of SEQ ID NO.: 9. Even more preferably, said sequence is at least 85%, 90%, 95%, 98% or 99% identical to the sequence of SEQ ID NO.: 9. Likewise comprised is the sequence of SEQ ID NO.: 10 or a sequence which is at least 70% identical to the sequence of SEQ ID NO.: 10. Preferably, said sequence is at least 75% identical to SEQ ID NO.: 10. More preferably, said sequence is at least 80% identical to the sequence of SEQ ID NO.: 10. Even more preferably, said sequence is at least 85%, 90%, 95%, 98% or 99% identical to the sequence of SEQ ID NO.: 10. Also comprised is the sequence of SEQ ID NO.: 11 or a sequence which is at least 70% identical to the sequence of SEQ ID NO.: 11. Preferably, said sequence is at least 75% identical to sequence SEQ ID NO.: 11. More preferably, said sequence is at least 80% identical to the sequence of SEQ ID NO.: 11. Even more preferably, said sequence is at least 85%, 90%, 95%, 98% or 99% identical to the sequence of SEQ ID NO.: 11. Furthermore comprised is the sequence of SEQ ID NO.: 12 or a sequence which is at least 60% identical to the sequence of SEQ ID NO.: 12. Preferably, said sequence is at least 65% identical to SEQ ID NO.: 12. More preferably, said sequence is at least 70% identical to the sequence of SEQ ID NO.: 12. Even more preferably, said sequence is at least 75% or 80% identical to SEQ ID NO.: 12. Particularly preferably, said sequence is at least 85%, 90%, 95%, 98% or 99% identical to the sequence of SEQ ID NO.: 12. Likewise comprised is the sequence of SEQ ID NO.: 13 or a sequence which is at least 60% identical to the sequence of SEQ ID NO.: 13. Preferably, said sequence is at least 65% identical to SEQ ID NO.: 13. More preferably, said sequence is at least 70% identical to the sequence of SEQ ID NO.: 13. Even more preferably, said sequence is at least 75% or 80% identical to SEQ ID NO.: 13. Particularly preferably, said sequence is at least 85%, 90%, 95%, 98% or 99% identical to the sequence of SEQ ID NO.: 13. Also comprised is the sequence of SEQ ID NO.: 14 or a sequence which is at least 75% identical to the sequence of SEQ ID NO.: 14. Preferably, said sequence is at least 80% identical to the sequence of SEQ ID NO.: 14. More preferably, said sequence is at least 85% identical to the sequence of SEQ ID NO.: 14. Even more preferably, said sequence is at least 90%, 95%, 98% or 99% identical to the sequence of SEQ ID NO.: 14. Additionally comprised is the sequence of SEQ ID NO.: 15 or a sequence which is at least 95% identical to the sequence of SEQ ID NO.: 15. Preferably, said sequence is at least 98% or 99% identical to the sequence of SEQ ID NO.: 15. Also comprised is the sequence of SEQ ID NO.: 16 or a sequence which is at least 95% identical to the sequence of SEQ ID NO.: 16. Preferably, said sequence is at least 98% or 99% identical to the sequence of SEQ ID NO.: 16. Furthermore comprised is the sequence of SEQ ID NO.: 17 or a sequence which is at least 75% identical to the sequence of SEQ ID NO.: 17. Preferably, said sequence is at least 80% identical to the sequence of SEQ ID NO.: 17. More preferably, said sequence is at least 85% identical to the sequence of SEQ ID NO.: 17. Even more preferably, said sequence is at least 90%, 95%, 98% or 99% identical to the sequence of SEQ ID NO.: 17. Likewise comprised is the sequence of SEQ ID NO.: 18 or a sequence which is at least 70% identical to the sequence of SEQ ID NO.: 18. Preferably, said sequence is at least 75% identical to SEQ ID NO.: 18. More preferably, said sequence is at least 80% identical to the sequence of SEQ ID NO.: 18. Even more preferably, said sequence is at least 85%, 90%, 95%, 98% or 99% identical to the sequence of SEQ ID NO.: 18. Also comprised is the sequence of SEQ ID NO.: 19 or a sequence which is at least 70% identical to the sequence of SEQ ID NO.: 19. Preferably, said sequence is at least 75% identical to SEQ ID NO.: 19. More preferably, said sequence is at least 80% identical to the sequence of SEQ ID NO.: 19. Even more preferably, said sequence is at least 85%, 90%, 95%, 98% or 99% identical to the sequence of SEQ ID NO.: 19. Additionally comprised is the sequence of SEQ ID NO.: 20 or a sequence which is at least 60% identical to the sequence of SEQ ID NO.: 20. Preferably, said sequence is at least 65% identical to SEQ ID NO.: 20. More preferably, said sequence is at least 70% identical to the sequence of SEQ ID NO.: 20. Even more preferably, said sequence is at least 75% or 80% identical to SEQ ID NO.: 20. Particularly preferably, said sequence is at least 85%, 90%, 95%, 98% or 99% identical to the sequence of SEQ ID NO.: 20. Also comprised is the sequence of SEQ ID NO.: 21 or a sequence which is at least 90% identical to the sequence of SEQ ID NO.: 21. Preferably, said sequence is at least 95% identical to the sequence of SEQ ID NO.: 21. More preferably, said sequence is at least 98% or 99% identical to the sequence of SEQ ID NO.: 21. Furthermore comprised is the sequence of SEQ ID NO.: 22 or a sequence which is at least 70% identical to the sequence of SEQ ID NO.: 22. Preferably, said sequence is at least 75% identical to SEQ ID NO.: 22. More preferably, said sequence is at least 80% identical to the sequence of SEQ ID NO.: 22. Particularly preferably said sequence is at least 85%, 90%, 95%, 98% or 99% identical to the sequence of SEQ ID NO.: 22. Likewise comprised is the sequence of SEQ ID NO.: 23 or a sequence which is at least 55% identical to the sequence of SEQ ID NO.: 23. Preferably, said sequence is at least 60% identical to SEQ ID NO.: 23. More preferably, said sequence is at least 65% identical to the sequence of SEQ ID NO.: 23. Even more preferably, said sequence is at least 70% or 75% identical to SEQ ID NO.: 23. Particularly preferably, said sequence is at least 80%, 85%, 90%, 95%, 98% or 99% identical to the sequence of SEQ ID NO.: 23. Also comprised is the sequence of SEQ ID NO.: 24 or a sequence which is at least 65% identical to the sequence of SEQ ID NO.: 24. Preferably, said sequence is at least 70% identical to SEQ ID NO.: 24. More preferably, said sequence is at least 75% identical to the sequence of SEQ ID NO.: 24. Even more preferably, said sequence is at least 80% or 85% identical to SEQ ID NO.: 24. Particularly preferably, said sequence is at least 90%, 95%, 98% or 99% identical to the sequence of SEQ ID NO.: 24. Furthermore comprised is the sequence of SEQ ID NO.: 25 or a sequence which is at least 55% identical to the sequence of SEQ ID NO.: 25. Preferably, said sequence is at least 60% identical to SEQ ID NO.: 25. More preferably, said sequence is at least 65% identical to the sequence of SEQ ID NO.: 25. Even more preferably, said sequence is at least 70% or 75% identical to SEQ ID NO.: 25. Particularly preferably, said sequence is at least 80%, 85%, 90%, 95%, 98% or 99% identical to the sequence of SEQ ID NO.: 25. Also comprised is the sequence of SEQ ID NO.: 26 or a sequence which is at least 55% identical to the sequence of SEQ ID NO.: 26. Preferably, said sequence is at least 60% identical to SEQ ID NO.: 26. More preferably, said sequence is at least 65% identical to the sequence of SEQ ID NO.: 26. Even more preferably, said sequence is at least 70% or 75% identical to SEQ ID NO.: 26. Particularly preferably, said sequence is at least 80%, 85%, 90%, 95%, 98% or 99% identical to the sequence of SEQ ID NO.: 26. Likewise comprised is the sequence of SEQ ID NO.: 27 or a sequence which is at least 55% identical to the sequence of SEQ ID NO.: 27. Preferably, said sequence is at least 60% identical to SEQ ID NO.: 27. More preferably, said sequence is at least 65% identical to the sequence of SEQ ID NO.: 27. Even more preferably, said sequence is at least 70% or 75% identical to SEQ ID NO.: 27. Particularly preferably, said sequence is at least 80%, 85%, 90%, 95%, 98% or 99% identical to the sequence of SEQ ID NO.: 27. Furthermore comprised is the sequence of SEQ ID NO.: 28 or a sequence which is at least 75% identical to the sequence of SEQ ID NO.: 28. Preferably, said sequence is at least 80% identical to SEQ ID NO.: 28. More preferably, said sequence is at least 85% identical to the sequence of SEQ ID NO.: 28. Even more preferably, said sequence is at least 90%, 95%, 98% or 99% identical to SEQ ID NO.: 28. Likewise comprised is the sequence of SEQ ID NO.: 29 or a sequence which is at least 70% identical to the sequence of SEQ ID NO.: 29. Preferably, said sequence is at least 75% identical to SEQ ID NO.: 29. More preferably, said sequence is at least 80% identical to the sequence of SEQ ID NO.: 29. Even more preferably, said sequence is at least 85% or 90% identical to SEQ ID NO.: 29. Particularly preferably, said sequence is at least 95%, 98% or 99% identical to the sequence of SEQ ID NO.: 29. Also comprised is the sequence of SEQ ID NO.: 30 or a sequence which is at least 60% identical to the sequence of SEQ ID NO.: 30. Preferably, said sequence is at least 65% identical to SEQ ID NO.: 30. More preferably, said sequence is at least 70% identical to the sequence of SEQ ID NO.: 30. Even more preferably, said sequence is at least 75% or 80% identical to SEQ ID NO.: 30. Particularly preferably, said sequence is at least 85%, 90%, 95%, 98% or 99% identical to the sequence of SEQ ID NO.: 30. Furthermore comprised is the sequence of SEQ ID NO.: 31 or a sequence which is at least 55% identical to the sequence of SEQ ID NO.: 31. Preferably, said sequence is at least 60% identical to SEQ ID NO.: 31. More preferably, said sequence is at least 65% or 70% identical to the sequence of SEQ ID NO.: 31. Even more preferably, said sequence is at least 75% or 80% identical to SEQ ID NO.: 31. Particularly preferably, said sequence is at least 85%, 90%, 95%, 98% or 99% identical to the sequence of SEQ ID NO.: 31. Likewise comprised is the sequence of SEQ ID NO.: 32 or a sequence which is at least 55% identical to the sequence of SEQ ID NO.: 32. Preferably, said sequence is at least 60% identical to SEQ ID NO.: 32. More preferably, said sequence is at least 65% or 70% identical to the sequence of SEQ ID NO.: 32. Even more preferably, said sequence is at least 75% or 80% identical to SEQ ID NO.: 32. Particularly preferably, said sequence is at least 85%, 90%, 95%, 98% or 99% identical to the sequence of SEQ ID NO.: 32. Furthermore comprised is the sequence of SEQ ID NO.: 33 or the sequence of SEQ ID NO.: 34. The amino acid sequences mentioned and characterized by SEQ IDs are preferably encoded by the DNA sequences referred to as SEQ ID numbers 35 to 68. Preference is further given to polypeptides which correspond to the naturally occurring enzymes over their full length. In another preferred embodiment, the polypeptides of the invention additionally comprise at least one heterologous amino acid section which characterizes said polypeptides as fusion proteins. Possible examples of heterologous components of the fusion protein of the invention are Tags (e.g. His-Tag or Flag-Tag) which may be used for purification of the fusion proteins of the invention. In other embodiments, the heterologous components may have their own enzymic activity. In such a case, the two enzymic components are preferably linked by a linker such as a flexible glycine or glycine-serine linker of 6-10 amino acids in length, in order to ensure the functionality of said components. The term "heterologous", as used herein, may mean, firstly, that the components of the fusion protein do not naturally occur covalently linked together and, secondly, that the components originate from different species. Fusion proteins are usually prepared using recombinant DNA technology (see Sambrook et al., loc. cit.).

According to the invention, the term "polypeptide which has the biological activity of an NAD- or NADP-dependent alcohol dehydrogenase" refers to a group of enzymes which catalyze the conversion of alcohols to aldehydes or ketones or the corresponding reverse reaction, i.e. the conversion of aldehydes to primary alcohols or ketones to secondary alcohols. The first-mentioned reaction corresponds in this connection to an oxidative process, with the secondly mentioned type of reaction being a reductive process. The EC number of alcohol dehydrogenases (ADHs) is EC 1.1.1.1. The scope of protection of the invention comprises, in addition to the naturally occurring enzymes isolated in the course of the present invention, also those polypeptides which have the aforementioned identity values at the amino acid level compared to the polypeptides isolated from natural sources and which may likewise originate from natural sources. On the other hand, they may be modified by recombinant DNA technology in such a way that the enzymic activity is retained or essentially retained, as will be anticipated by the skilled worker (cf., for example, Sambrook et al, "Molecular Cloning, A Laboratory Handbook", 2nd edition 1989, CSH Press, Cold Spring Harbor, Ausubel et al. "Current Protocols in Molecular Biology", John Wiley & Sons, NY 2001). Thus, it is possible for amino acids which are not located at the active site and whose replacement with an amino acid "of the same kind" is not expected at first sight to result in a substantially altered three-dimensional structure to be replaced with an amino acid "of the same kind". For example, particular amino acids with nonpolar side chains (amino acids of the same kind), may be expected to be able to be substituted, for example valine for alanine, without this having a (substantial) influence on the biological function of the enzyme, on the enzymic activity in accordance with the invention. On the basis of his specialist knowledge, the skilled worker may draw corresponding conclusions also for the substitution of other types of amino acids (for example the replacement of basic amino acids with other basic amino acids or of amino acids with uncharged polar side chains with other amino acids from this group).

The percentage of identity to the amino acid sequences of the polypeptides isolated from natural sources, which are described in this description by SEQ ID numbers, may be readily determined by the skilled worker using processes known in the prior art. A suitable program which may be used according to the invention is BLASTP (Altschul et al. 1997. Gapped BLAST and PSI-BLAST: a new generation of protein database search programs. Nucleic Acids Res. 25(17): 3389-3402.).

The invention also relates to a nucleic acid molecule which encodes the polypeptide of the invention.

The nucleic acid molecule of the invention may be a DNA molecule or an RNA molecule. Preference is given to the nucleic acid molecule being a cDNA molecule or an mRNA molecule. According to the invention, said DNA molecule may furthermore be a genomic DNA molecule. The invention also comprises embodiments in which said DNA molecule is a PNA molecule or another derivative of a DNA molecule. According to the invention, preference is given to DNA sequences comprising the DNA sequences according to SEQ ID numbers 35 to 68.

In order to achieve the object on which the invention is based, the following approach was pursued. Firstly, based on an extensive proprietary strain collection, prioritized strains were grown on plates and, after viability and purity controls had been carried out, also in liquid culture. The genomic DNA of these organisms was isolated from the harvested cell pellets. Based on the genomic DNA prepared, selected isolates were genetically screened for alcohol dehydrogenase genes via PCR typing by means of primers of the invention. In this context, even the amino acid sequence similarity due to homology of already known alcohol dehydrogenases did not readily allow oligonucleotide primers to be derived with the aid of which previously unidentified alcohol dehydrogenase genes may readily be amplified successfully. Initially, this approach was based on the hypothesis of particular sequence motifs conserved in the previously known alcohol dehydrogenase genes also being present in the desired novel alcohol dehydrogenase genes. However, the sequence motifs conserved in the previously known alcohol dehydrogenase genes are unsuitable for deriving degenerated primers by processes known to the skilled worker (Kwok et al. 1995. Design and use of mismatched and degenerate primers. In: PCR Primer A laboratory Manual, Dieffenbach C W & Dveksler G S (Editors), Cold Spring Harbor Laboratory Press, pp 143-155; Compton T. 1990. Degenerate Primers for DNA Amplification. In: PCR Protocols, A Guide to Methods and Applications. Innis et al. (Editors) Academic Press, San Diego, pp 39-34). The NAD- or NADP-dependent alcohol dehydrogenases are classified as long-chain, medium-chain and short-chain ADHs. They are divided into these three groups especially based on their metal dependence and the size of subunits. The short-chain ADHs do not require any metal ions and their subunits consist of approximately 250 amino acids. In contrast, the medium-chain and long-chain ADHs are dependent on metal ions. The medium-chain ones whose typical subunits consist of approx. 350 amino acids require zinc ions. The long-chain ADHs whose subunits are composed of approx. 385 amino acids require iron ions (Hummel, W. 1997. New alcohol dehydrogenases for the synthesis of chiral compounds. 58:145-84). The sequence heterogeneity, not only within all of the previously known NAD- or NADP-dependent ADHs but also within the three ADH groups briefly described above, is extremely high. Therefore, it was not that easy to construct primers with the aid of which it is possible firstly to amplify specifically ADH sequences and secondly also to capture a diversity of novel ADHs necessary in order to achieve the object. Thus, despite the sequence homologies expected on the basis of the used, no long-chain ADHs whatsoever were isolated in the bacteria studied. In this connection, it was intended to test the quality of the constructed primers first with genomic DNA of model organisms whose alcohol dehydrogenase genes are known or with DNA pools consisting of DNA from various microorganisms. This involved cloning, sequencing and subsequently analyzing PCR products. After this establishing phase, selected isolates were subjected to PCR typing on the basis of the prepared genomic DNA of the microorganisms to be screened, as described above. The results obtained from the experiments (regarding sequence identity and specific activity) were incorporated into prioritizing the potential Hit organisms whose novel alcohol dehydrogenase genes are being isolated. Despite the unexpected, disappointing and demotivating results in the course of the attempted isolation of nucleic acids supposed to encode long-chain ADHs, a number of nucleic acids encoding short-chain enzymes and medium-chain enzyme chains were isolated according to the invention. Some of these enzymes and enzyme chains had surprisingly low sequence identities (<50%) to the known enzymes of this class.

The invention furthermore relates to a nucleic acid molecule which is complementary to the nucleic acid molecule of the invention.

According to the invention, the term "complementary" means a complementarity which extends across the entire region of the nucleic acid molecule of the invention without gaps. In other words, preference is given according to the invention to said complementarity extending 100% across the entire region of the sequence of the invention, i.e. from the 5' end shown to the 3' end shown. In further preferred embodiments, said complementarity extends across a region of at least 19, preferably at least 21, contiguous nucleotides which preferably do not code for the active site of enzymic activity.

In addition, the invention relates to a vector which comprises the nucleic acid molecule of the invention.

The vectors of the invention preferably contain the nucleic acids of the invention operatively linked to an expression control sequence so as for said nucleic acids to be able to be transcribed and, where appropriate, translated in a suitable host cell. Expression control sequences usually comprise a promoter and, where appropriate, further regulatory sequences such as operators or enhancers. Furthermore, translation initiation sequences may also be present. Suitable expression control sequences for prokaryotic or eukaryotic host cells are known to the skilled worker (see, for example, Sambrook et al., loc. cit.). The recombinant vector of the invention may furthermore also contain usual elements such as an origin of replication and a selection marker gene. Examples of suitable recombinant vectors are plasmids, cosmids, phages or viruses (see, for example, Sambrook et al., supra). Starting materials for preparing the recombinant vectors of the invention are commercially available (for example from Stratagene, InVitroGen or Promega).

Any plasmids or vectors available to the skilled worker for this purpose are suitable in principle. Plasmids and vectors of this kind may be found, for example, in Studier and coworkers (Studier, W. F.; Rosenberg A. H.; Dunn J. J.; Dubendroff J. W.; (1990), Use of the T7 RNA polymerase to direct expression of cloned genes, Methods Enzymol. 185, 61-89) or in the brochures from Novagen, Promega, New England Biolabs, Clontech or Gibco BRL. Further preferred plasmids and vectors may be found in: Glover, D. M. (1985), DNA cloning: a practical approach, Vol. I-III, IRL Press Ltd., Oxford; Rodriguez, R. L. and Denhardt, D. T (eds) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York. Plasmids which may be used for cloning the gene construct having the nucleic acid of the invention into the host organism in a very preferred manner are derivatives of: pUC18 and pUC19 (Roche Biochemicals), pKK-177-3H (Roche Biochemicals), pBTac2 (Roche Biochemicals), pKK223-3 (Amersham Pharmacia Biotech), pKK-233-3 (Stratagene) or pET (Novagen). Other preferred plasmids are pBR322 (DSM3879), pACYC184 (DSM4439) and pSC101 (DSM6202), which may be obtained from the DSMZ-Deutsche Sammlung von Mikroorganismen und Zellkulturen GmbH, Brunswick, Germany. Examples of preferred promoters are T7, lac, tac, trp, rha and ara.

The invention also relates to a nonhuman host which comprises the polypeptide of the invention or the nucleic acid molecule of the invention or the vector of the invention.

The nonhuman host may be a cell or a multi- to polycellular organism. Suitable polycellular organisms include model systems familiar in molecular biology, such as *Drosophila melanogaster*, zebra fish or *C. elegans*.

In a preferred embodiment, the host is a cell.

In this preferred embodiment, the host of the invention is a recombinant cell which has been transformed or transfected with a nucleic acid of the invention or a vector of the invention (according to the present invention, the terms "transformation" and "transfection" are used synonymously). Transformation or transfection may be carried out by known methods, for example calcium phosphate coprecipitation, lipofection, electroporation, particle bombardment or viral infection. The cell of the invention may contain the recombinant nucleic acid in an extrachromosomal or a chromosomally integrated form. In other words, the transfection/transformation may be stable or transient.

The recombinant cell preferably is of prokaryotic origin. Suitable host cells include cells of unicellular microorganisms, such as bacteria cells. A particularly suitable bacterial host system is *E. coli*. The cytoplasm of *E. coli* contains the cofactors required for the enzymic activity of the polypeptide of the invention. These are, in particular, NADH, NADPH, $NAD^+$ and $NADP^+$. Very particular preference is given to: *E. coli* XL1 Blue, W3110, DSM14459 (PCT/US00/08159), NM 522, JM101, JM109, JM105, RR1, DH5, TOP 10- or HB101. It is also possible to use for expression of the nucleic acids of the invention bacteria of the genera/species *Lactobacillus*, Bacillus, Rhodococus, Campylobacter, Caulobacter, Mycobacterium, Streptomyces, Neisseria, Ralstoni, Pseudomonas, and Agrobacterium. Appropriate strains are available in the prior art and may, at least partially, be obtained via the international deposition sites such as ATCC or DMSZ. Transfection protocols and transformation protocols are known to the skilled worker. (Chan and Cohen. 1979. High Frequency Transformation of Bacillus subtilis Protoplasts by Plasmid DNA. Mol Gen Genet. 168(1):111-5; Kieser et al. 2000. Practical Streptomyces Genetics. The John Innes Foundation Norwich.; Sambrook et al. 1989. Molecular Cloning. A Laboratory Manual. In: second ed. Cold Spring Harbor Laboratory Press. Cold Spring Harbor. NY.; Irani and Rowe. 1997. Enhancement of transformation in Pseudomonas aeruginosa PAO1 by $Mg^{2+}$ and heat. Biotechniques 22: 54-56). Additional examples of host organisms which may be used are also yeasts such as Hansenula polymorpha, Pichia sp., Saccharomyces cerevisiae. As an alternative to this, the cell may be of eukaryotic origin. Suitable eukaryotic cells include CHO cells, HeLa cells and others. Many of these cells are obtainable via deposition sites such as ATCC or DMSZ.

In a further preferred embodiment, the host is a transgenic nonhuman animal.

Transgenic nonhuman animals may be produced by processes known in the prior art.

The transgenic nonhuman animal of the invention may preferably have various genetic constitutions. It may (i) constitutively or inducibly overexpress the gene of a nucleic acid of the invention, (ii) contain the endogenous gene of a nucleic acid of the invention in an inactive form, (iii) contain the endogenous gene of a nucleic acid of the invention completely or partially replaced with a mutated gene of a nucleic acid of the invention, (iv) have conditional and tissue-specific overexpression or underexpression of the gene of a nucleic acid of the invention or (v) have a conditional and tissue-specific knock-out of the gene of a nucleic acid of the invention. Preferably, the transgenic animal additionally contains an exogenous gene of a nucleic acid of the invention under the control of a promoter allowing overexpression. Alternatively, the endogenous gene of a nucleic acid of the invention may be overexpressed by activating or/and replacing the intrinsic promoter. Preferably, the endogenous promoter of the gene of a nucleic acid of the invention has a genetic modification which results in increased expression of the gene. Said genetic modification of the endogenous promoter here comprises both a mutation of individual bases and deletion and insertion mutations.

In a particularly preferred embodiment of the host of the invention, the latter is a transgenic rodent, preferably a transgenic mouse, a transgenic rabbit, a transgenic rat, or is a transgenic sheep, a transgenic cow, a transgenic goat or a transgenic pig.

Mice have numerous advantages over other animals. They can be kept easily and their physiology is regarded as a model system for that of humans. The production of such gene-manipulated animals is sufficiently known to the skilled worker and carried out using common processes (see, for example, Hogan, B., Beddington, R., Costantini, F. and Lacy, E. (1994), Manipulating the Mouse-Embryo; A Laboratory Manual, 2nd ed., Cold Spring Harbor Laboratory, Cold Spring Harbor, N.Y.; WO91/08216). Alternatively or additionally, it is also possible to employ cell culture systems, in particular human cell culture systems, for the applications described for the nonhuman transgenic animal of the invention.

Examples of cofactors of alcohol dehydrogenases, which are used—as already mentioned, depending on the particular alcohol dehydrogenase—are NADH and NADPH and their oxidized forms, $NAD^+$ and $NADP^+$, respectively.

The cofactors may be regenerated, in principle, either in an enzyme-coupled manner using a second enzyme, for example a formate dehydrogenase or glucose dehydrogenase, or in a substrate-coupled manner using any of the alcohols accepted as substrate by the alcohol dehydrogenase employed, for example—iso-propanol—if accepted as substrate. The diagram below indicates by way of example the concept of the alcohol dehydrogenase-catalyzed reduction of a ketone with enzyme-coupled cofactor regeneration using a formate dehydrogenase.

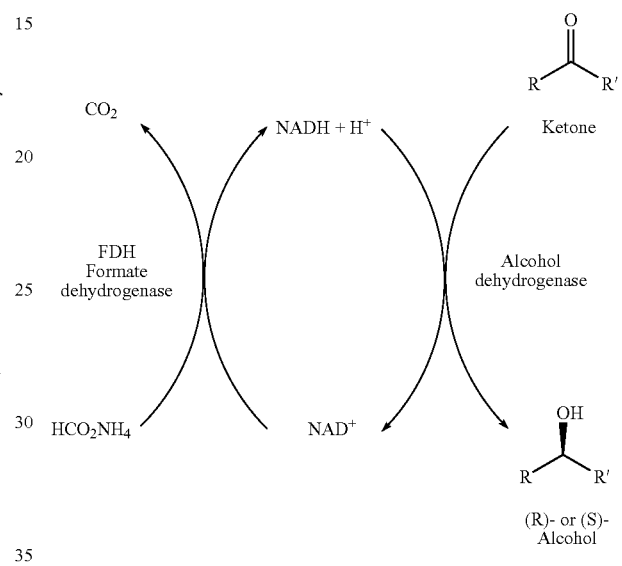

Alcohol dehydrogenases are used, for example, for preparing enantiomerically enriched, preferably enantiomerically pure, secondary alcohols, starting from prochiral ketones. In this connection, both (R)- and (S)-specific alcohol dehydrogenases are known which accordingly result in the formation of the particular enantiomeric (R) and, respectively, (S) forms of alcohols.

Correspondingly, preference is also given according to the invention to a host which has a further dehydrogenase suitable for cofactor regeneration or a nucleic acid molecule encoding said dehydrogenase.

In this connection, the host may contain naturally said further dehydrogenase or may have been transfected with a recombinant nucleic acid which encodes said dehydrogenase and with which it is possible to express said dehydrogenase in said host. This embodiment also requires the host having the cofactors necessary for the function of said further dehydrogenase or said cofactors being delivered to said host in a suitable manner.

Particular preference is given in this connection to a host in which the dehydrogenase suitable for cofactor regeneration is a formate dehydrogenase or a glucose dehydrogenase. Particular preference is given to a Candida boidinii formate dehydrogenase. Particular preference is also given to the cofactor-regenerating dehydrogenase being a Bacillus subtilis glucose dehydrogenase. Genetically modified mutants of said cofactor-regenerating dehydrogenases, which retain said enzymic function, are likewise preferred according to the invention.

In a further embodiment, the invention relates to a reaction system which comprises an organic compound which is a substrate of a dehydrogenase, furthermore the polypeptide of the invention, the vector of the invention or the host of the invention and, where appropriate, a cofactor for the polypeptide of the invention. (The addition of cofactor is required in those cases in which the cofactor is not already present in the system, see also hereinbelow). In one case, the reaction system of the invention may be a bacterial cell which corresponds to the host of the invention and which has the polypeptide of the invention and also the necessary cofactors in the cytoplasm. In the case of the cofactor(s) already being present naturally in the system/host, said cofactors need no longer be delivered separately. Suitably, the host is one which has a further dehydrogenase suitable for cofactor regeneration or a nucleic acid molecule encoding said dehydrogenase and also the cofactors required therefore. If a substrate for a desired product is supplied to said reaction system or if said substrate is metabolized in the reaction system itself, then the desired product may readily be isolated from the reaction system, if said reaction system is maintained under suitable conditions. Suitable conditions include carrying out the reaction at temperatures of from 10 to 80° C., preferably from 20 to 60° C., and very preferably from 20 to 40° C. Preference is also given to the substrate concentration being from 100 to 2000 mM, preferably from 200 to 800 mM. In a preferred form, the desired reaction is carried out so as to achieve conversions of >80%, in particular >90%, within a reaction time of <20 hours, in particular a reaction time of <10 hours and very preferably a reaction time of <5 hours. In another embodiment, the reaction system may be an in vitro system for converting a suitable substrate to obtain the desired product. For example, the polypeptide of the invention may be contacted with the cofactors mentioned and the substrate and, where appropriate (i.e. if necessary), with a further dehydrogenase suitable for cofactor regeneration (and, where appropriate, cofactors required therefore, in particular NADH and/ or NADPH their oxidized forms) under suitable conditions, as set out above, for example, and over a sufficient period of time, so that the desired product may be generated. In this in vitro variant with utilization of isolated enzymes (in purified form or as crude extract) and addition of cofactors, these cofactor additions should, in accordance with an economical process control, be <0.01 equivalents (based on the amount of substrate employed), preferably <0.001 equivalents and very preferably <0.0005 equivalents.

The "reaction system" may moreover also be a transgenic nonhuman animal to which a suitable substrate and, where appropriate, cofactors or/and said further dehydrogenase is fed or administered and which is capable of converting said substrate in suitable tissues. In another embodiment, the reaction system may also be a cellular membrane system in which the enzyme, the enzymes and, where appropriate, the cofactors are anchored.

Further preference is given according to the invention to a reaction system in which the organic compound which is a substrate of a dehydrogenase is a carbonyl compound.

Particular preference is given to a reaction system in which the carbonyl compound is an aldehyde or a ketone.

This embodiment of the invention permits the preparation, particularly preferred according to the invention, of technical grade alcohols which may be used, for example, as intermediates for the preparation of active compounds usable in medicaments.

Particular preference is given according to the invention to the ketone being an asymmetrically substituted ketone.

This embodiment of the invention is particularly preferred because the products generated in a corresponding reduction have a center of chirality and may be obtained with high enantioselectivity. In general, the desired chiral secondary alcohols are obtained in an enantiomerically pure form with an enantiomeric excess of >99%.

In another preferred embodiment of the reaction system of the invention, the organic compound which is a substrate of a dehydrogenase is an alcohol. This variant is preferably suitable for preparing commercially important carbonyl compounds, for example ketones relevant in the field of aroma chemicals. In addition, oxidation may also be utilized for the formation of enantiomerically pure, secondary alcohols by starting from a racemic alcohol as substrate and converting the undesired enantiomer into the ketone compound by enantioselective oxidation. The remaining, desired enantiomer may then be isolated accordingly.

The alcohol is preferably a primary alcohol or a chiral secondary alcohol. In the first case, the product generated is an aldehyde, whereas in the second case the corresponding ketones are formed.

Preference is also given according to the invention to the cofactor in the reaction system of the invention being NADH, NADPH, NAD$^+$ or NADP$^+$.

The invention also relates to a process for preparing the polypeptide of the invention or a polypeptide encoded by the nucleic acid molecule of the invention, which process comprises growing the host of the invention and isolating said polypeptide.

The polypeptide may be purified, for example, by conventional processes, for example by disrupting appropriate cells, for example by means of a "French press", by ion exchange, size selection or affinity chromatography etc. (Coligan et al. Current Protocols in Protein Science, John Wiley & Sons, Inc.). As an alternative to this, the polypeptide of the invention, when linked to a leader peptide, may be exported out of the cells and purified from the culture supernatant. This embodiment requires the polypeptide of the invention, which does not naturally contain a leader peptide, to be genetically modified. This embodiment has the advantage of a simpler purification of the polypeptide of the invention from the culture supernatant. The best procedures and suitable leader peptides may be readily determined by the skilled worker.

In a further preferred embodiment of the process of the invention, the polypeptide is isolated from a body fluid or tissue sample of the nonhuman transgenic animal. In this embodiment too, the polypeptide of the invention preferably contains a leader peptide.

In a further preferred embodiment of the process of the invention and, in particular, if the nonhuman transgenic animal is a mammal, for example a cow, a goat or a sheep, the body fluid is milk or serum.

In another embodiment, the invention relates to a process for preparing an organic compound which is a product of a dehydrogenase, which process comprises reacting an organic compound which is a substrate of a dehydrogenase with the polypeptide of the invention, the host of the invention or by means of the reaction system of the invention.

The various embodiments of the invention which are to be used in the process of the invention differ in principle in that further components such as cofactors etc. (cf. supra) have to be added to the polypeptide, if the latter is used in a cell-free in vitro system. When using the reaction system of the invention, the necessary components, with the possible exception of the substrate, are preferably and advantageously already present in the system, and a separate addition is thus not needed here.

Preference is given according to the invention to a process which further comprises the step of isolating the product of the reaction. Suitable processes for isolation/purification have been set forth above.

In a particularly preferred embodiment of the process of the invention, the latter further comprises processing the product to give a medicament. A number of descriptions of utilizing enantiomerically pure alcohols as intermediates for preparing pharmaceutical active compounds are given in the literature. An overview in this respect is contained, inter alia, in: A. Kleemann, J. Engels, B. Kutscher, D. Reichert, Pharmaceutical Substances: Syntheses, patents, applications, 4th edition, Thieme-Verlag, Stuttgart, 2001.

In another, particularly preferred embodiment of the process of the invention, the latter further comprises the step of processing the product to give a secondary product. In this connection, derivatization may take place both by way of modification of the alcohol group, for example by esterification and subsequent secondary reactions, and by way of modifications of the particular substituents.

Particular preference is given here to the process of the invention further comprising the step of formulating the secondary product with a pharmaceutically compatible carrier or excipient or diluent in the preparation of a medicament.

Examples of suitable pharmaceutically compatible carriers and/or diluents are known to the skilled worker and comprise, for example, phosphate-buffered saline solutions, water, emulsions such as, for example, oil/water emulsions, various types of wetting agents or detergents, sterile solutions, etc. Medicaments comprising such carriers may be formulated by means of known conventional methods. Said medicaments may be administered in a suitable dose to an individual. The administration may be carried out orally or parenterally, for example intravenously, intraperitoneally, subcutaneously, intramuscularly, locally, intranasally, intrabronchially, orally or intradermally, or via a catheter at a site in an artery. Preparations for parenteral administration comprise sterile aqueous or nonaqueous solutions, suspensions and emulsions. Examples of nonaqueous solvents are propylene glycol, polyethylene glycol, vegetable oils such as, for example, olive oil, and organic ester compounds such as, for example, ethyl oleate, which are suitable for injections. Aqueous carriers comprise water, alcohol/water-based solutions, emulsions, suspensions, salt solutions and buffered media. Parenteral carriers comprise sodium chloride solutions, Ringer dextrose, dextrose and sodium chloride, Ringer lactate and bound oils. Examples of intravenous carriers include liquid, nutrient and electrolyte supplements (such as, for example, those based on Ringer dextrose). The medicament may moreover comprise preservants and other additives such as, for example, antimicrobial compounds, antioxidants, complexing agents and inert gases. Depending on the intended specific usage, other active compounds such as, for example, interleukins, growth factors, differentiation factors, interferons, chemotactic proteins or an unspecific immunomodulating agent, may also be included.

The type of dosage is determined by the attending physician according to the clinical factors. The skilled worker knows that the type of dosage depends on various factors such as, for example, body size or weight, body surface area, age, sex or general health of the patient, or else on the agent to be specially administered, duration and type of administration, and on other medicaments which may be administered in parallel. A typical dose may be, for example, in a range between 0.001 and 1000 µg, with doses being conceivable below and above this exemplary range, especially when taking into account the abovementioned factors. If the composition of the invention is administered regularly, the unit dose per day should generally be in a range between 1 µg and 10 mg. The active compounds in these preparations are usually present at a concentration of more than 10 µg/ml of a physiological buffer. However, they may also be present in solid form at a concentration of from 0.1 to 99.5% by weight of the total mixture. In general, it has proven advantageous to administer the active compound(s) in total amounts of from about 0.001 to 100 mg/kg, preferably in total amounts of from about 0.01 to 10 mg/kg, of body weight per 24 hours, where appropriate as continuous infusion or in the form of a plurality of individual doses, in order to achieve the desired result. If the composition is administered intravenously, the unit dose per kilogram of body weight per day should be in a range between 1 µg and 10 mg. The medicament may be administered topically, locally or systemically.

Finally, particular preference is given according to the invention to a process in which the product is an enantiomerically pure alcohol.

The invention also relates to a ligand which specifically binds the polypeptide of the invention, which ligand is neither a substrate of said polypeptide, nor a cofactor thereof, nor a product converted thereby.

The term "specifically binds" means according to the invention that the ligand does not or essentially does not cross react with other polypeptides, including those having a similar primary sequence or a similar three-dimensional structure. Cross reactivity may be determined by processes known in the prior art (cf. Harlow and Lane "Antibodies, A Laboratory Manual", CSH Press, Cold Spring Harbor, 1988). To this end, it is possible to use, for example, competitive assays, for example turbidimetric tests, in which the ligand is incubated together with the labeled polypeptide of the invention and a polypeptide competing therewith, it being possible for the latter to be used at different concentrations.

In a preferred embodiment, the ligand of the invention is an antibody or a fragment or derivative thereof, an aptamer, or a low-molecular weight substance.

Antibody fragments comprise Fv, Fab and F(ab')$_2$ fragments. The derivatives include scFvs (Harlow and Lane, loc. cit.). Antibodies may be of polyclonal or monoclonal origin. In a particularly preferred embodiment of the receptor of the invention, said receptor is a monoclonal antibody.

According to the invention, "low molecular weight substances" are naturally occurring or artificially produced molecules having a molecular weight of from about 250 to 1000 Da, preferably 300 to 750 Da, particularly preferably 400 to 600 Da, or are modified molecules of said molecular weight, which have been derived from natural substances.

The claimed invention furthermore comprises a primer having a sequence depicted in Table 1.

In addition, the invention relates to a primer pair having sequences depicted in Table 1, with the first primer of said primer pair serving as a forward primer and the second primer of said primer pair serving as a reverse primer to amplify a DNA sequence.

The primer of the invention (in combination with a further suitable primer, preferably a further suitable primer listed in Table 1) and the primer pair of the invention may be used for amplification of the sequences of the invention, preferably by means of PCR or LCR. The primers and primer pairs, respectively, have been selected with great care from a multiplicity of potentially possible primers. Besides amplification of the nucleic acid sequences of the invention, they also allow amplification of sequences which encode enzymes of the prior art, and are thus versatile.

The invention further relates to a kit comprising
the polypeptide of the invention;
the nucleic acid molecule of the invention;
the vector of the invention;
the host of the invention;
the ligand of the invention;
the reaction system of the invention;
at least one primer of the invention; and/or
at least one primer pair of the invention.

The components of the kit of the invention may be packaged individually or partly together in suitable vessels. The components may be present in the kit of the invention, for example, in freeze-dried form or, for example, in solution, with suitable solvents including in particular aqueous solvents such as buffered solutions, for example phosphate-buffered solutions.

The kits of the invention may be used in many different ways. For example, they may serve to identify further alcohol dehydrogenases or nucleic acids encoding these, with preference being given to using the primers of the invention. In other embodiments, the kits of the invention may be used for industrial production of the enzyme of the invention or of the products converted by said enzyme. In these embodiments, preference would be given to using the host of the invention or the reaction system of the invention.

In the Figures:

FIG. 1: depicts the prior art via the resolution of the racemate: at least 4-4 steps FIG. 2: depicts an overview of cluster 2 (=primer group 2), based on 33 sequences FIG. 3: depicts PCR typing with primer group 2, using various pools The examples illustrate the invention.

EXAMPLE 1

Clustering of ADHs and Primer Design

Strains were prioritized from an extensive proprietary strain collection and grown in liquid culture after carrying out viability and purity checks. Harvested cell pellets served as starting material for genetic screening. Primers for genetic screening for alcohol dehydrogenase genes were constructed and then tested on the basis of prepared genomic DNA of selected microbial isolates with the aid of PCR. NAD- or NADP-dependent alcohol dehydrogenases are classified as long-chain, medium-chain and short-chain ADHs. Since sequence heterogeneity within these groups is substantial, said groups were grouped in clusters based on sequence analyses. The long-chain ADHs were divided into three clusters, the medium-chain ADHs in 4 clusters and the short-chain ADHs in three clusters. Subsequently, in each case four degenerated primer sets per cluster were constructed which differ in the utilization of specific codons (codon usage) but which are directed against the same sequence motifs of the clusters.

EXAMPLE 2

Genetic Screening for Long-Chain Alcohol Dehydrogenases

The long-chain ADHs were divided on the basis of sequence analyses into three clusters and the primers were constructed and tested with an analogous procedure. However, despite expectations to the contrary, no PCR tags assignable to this group were amplified.

EXAMPLE 3

Genetic Screening for Medium-Chain Alcohol Dehydrogenases

Primers directed against medium-chain ADHs were designed as follows: the medium-chain ADHs were divided based on sequence analysis into four clusters. Subsequently, in each case four degenerated primer sets were constructed which differ by the selected codon usage. This will be illustrated graphically and by way of example in FIG. 2 on the basis of the group of organisms for determining the primer group 2. The primer sets were selected on the basis of conserved regions in 33 different alcohol dehydrogenase sequences.

These primer groups, for example primer group 2, were subsequently used for investigating various pools (containing genomic DNA from microorganisms). Using this primer set, it was possible to amplify, clone and sequence novel partial medium-chain ADH sequences. The corresponding result of this PCR typing is depicted below in FIG. 3. As documented, inter alia, by lanes 1, 2 and 10 in FIG. 3, in each case here gene sequences were found which indicate an alcohol dehydrogenase activity, owing to the gene sequence corresponding to known genes of ADH enzymes. Overall, further gene sequences with potential alcohol dehydrogenase activity were identified. The identity of the sequence tags found with already known ADHs was between 51-99%.

EXAMPLE 4

Genetic Screening for Special Medium-chain Alcohol Dehydrogenases, with Analogy to Alcohol Dehydrogenases from *Rhodococcus* Strains Owing to the interesting properties of the known *Rhodococcus erythropolis* (S)-alcohol dehydrogenase (S—Re-ADH; this enzyme is characterized by stereoselective conversion of a broad spectrum of ketones and ketoesters to the corresponding hydroxy compounds) which likewise belongs to the medium-chain alcohol dehydrogenases, and also of other alcohol dehydrogenases obtained from *Rhodococcus* strains, the question as to whether it is possible to identify novel ADH sequences exhibiting a relatively high similarity to this sequence with the aid of genetic screening, was looked into. The driving force here is the assumption that novel ADHs whose sequences share a high identity with the S—Re-ADH sequence could likewise possess interesting properties. For example, such novel ADHs could possess on the one hand the proven properties of S—Re-ADH but, on the other hand, for example, could have a modified substrate spectrum or increased expression performance. In order to answer the above question, comparative sequence analyses with the amino acid sequence of this S—Re-ADH were carried out first. These analyses revealed that S—Re-ADH is a representative of cluster 1 of the medium-chain ADHs. Furthermore, a group consisting of 5 protein sequences, which includes S—Re-ADH, was found within this cluster. Starting from these 5 sequences, degenerated primers were constructed and assayed, taking into account the codon usage, according to the procedure described above.

In order to reduce the number of PCRs to be carried out, pools consisting of 24 bacterial isolates were established and DNA was isolated. This DNA was used as template. Numerous sequence tags were amplified and sequenced. Analysis of the sequence tags translated into amino acid sequences revealed identities to the S—Re-ADH sequence of from about to Two full-length genes were isolated which are represented by one sequence tag and which exhibit 98% identity to S—Re-ADH at the amino acid sequence level. The novel ADHs are derived from the organism *Arthrobacter paraffineus* ATCC21317. The homology at the DNA level is 94%. Said full-length genes were isolated with the aid of a sequence homology approach.

EXAMPLE 5

Genetic Screening for Short-chain Alcohol Dehydrogenases

Moreover, 12 primer sets for the short-chain ADHs, which are directed against the three clusters of this group, were finally assayed. The template used was DNA which had been isolated from 5 isolates which, owing to their ADH activity, had reduced either 4-chloroacetophenone or 2-heptanone in the activity screening. The identity of the amino acid sequence tags to known short-chain ADH sequences is between and the vast majority of these sequences exhibiting an identity of less than to published sequences.

TABLE 1 sequences which were used for the screening of the DNA sequences encoding theac sof the invention

| Name | Sequence 5' → 3' | Direction | Block |
|---|---|---|---|
| ADHM1: | AAAGCATGCGGCGTTTGYCAYACNGA | Forward | A |
| ADHM2: | CCAATGTTTCATCGCTTGATATGBNG TRATNCC | Reverse | C |
| ADHM3: | TGCGGCGTCTGCCAYACBGA | Forward | A |
| ADHM4: | GCTTCAGGGCGTGGTAGGBVGTVAYR CC | Reverse | C |
| ADHM5: | GCGGCGTCTGCCACWCSGA | Forward | A |
| ADHM6: | GCTTCAGGGCCTGGTAGGBSGTSAYS CC | Reverse | C |
| ADHM7: | AGCCTGCGGCGTCTGYCAYWCBGA | Forward | A |
| ADHM8: | GCTTCAGCGCCTGGTAGGBSGTSAYN CC | Reverse | C |
| ADHM9: | GCAGCTTGCGGCATGTGYCAYACNGA | Forward | A |
| ADHM10: | GCCCAAGCCGGTCGTAAYNCCRCAN CC | Reverse | C |
| ADHM11: | GGCCTGCGGCATGTGYCAYACBGA | Forward | A |
| ADHM12: | CCCAAGCCGGTCGTGAYRMMRCAVCC | Reverse | C |
| ADHM13: | CCGGCATGTGCCACACSGA | Forward | A |
| ADHM14: | TGGCGGCCAGGCCSAYSSCSCC | Reverse | C |
| ADBM15: | GGCCTCCGGCATGTGYCAYACSGA | Forward | A |
| ADNM16: | TGGCGGCCAGGCCSAYNSCNCC | Reverse | C |
| ADHM17: | TTAAATGGTGCGGCATTTGYGGNWCN GA | Forward | A |
| ADHM18: | CAACTTAACAGCCAACATGCCDATNG KNCC | Reverse | D |

TABLE 1-continued sequences which were used for the screening of the DNA sequences encoding theac sof the invention

| Name | Sequence 5' → 3' | Direction | Block |
|---|---|---|---|
| ADHM19: | CAAGGTCAAGTGGTGCGGBATYTGY GG | Forward | A |
| ADHM20: | TGACGGCCAACATGCCRATNGKVCC | Reverse | D |
| ADHM21: | TGCGGCATCGGCGGSWCSGA | Forward | A |
| ADHM22: | CGAACTTGACGACGAAGAKSCCGATS GKSC | Reverse | D |
| ADHM23: | CAAGGTCAAGTGGTGCGGNATCTGY GG | Forward | A |
| ADHM24: | CGGCGAAGATGCCGATSGKNCC | Reverse | D |
| ADHM25: | GATTGTTAGAGTTACAGCTACAGCTA TTTGYGGNWSNGA | Forward | A |
| ADHM26: | TGAACGGCAAACAGGCCNAYNGGNCC | Reverse | D |
| ADHM27: | CGCCACCGCCATCTGYGGBWSBGA | Forward | A |
| ADHM28: | GACGGCGAACAGGCCNAYNGGVCC | Reverse | D |
| ADHM29: | CACCGCCATCTGCGGSWSSGA | Forward | A |
| ADHM30: | GGAGTGAACGGCGAACAKSCCSAYSG GSC | Reverse | D |
| ADHM31: | CGCCACCGCCATCTGYGGNWSBGA | Forward | A |
| ADHM32: | GACGGCGAACAGGCCSAYSGGNCC | Reverse | D |
| ADHM39 | AGAAGAACTGGGCATTATGCCNCCNG GNYT | Forward | A |
| ADHM40 | TGTATCAATTGTCGGTTGATAGCCNA CRAARTCNA | Reverse | D |
| ADHM41 | ACAACGTGGTCGTGTACGGNCCNTGG GG | Forward | |
| ADHM42 | GATGGTGGGCTGGTAGCCNACRAART CNA | Reverse | |
| ADHM43 | GACAACGTCGTCGTCTACGGNCCNTG GGG | Forward | |
| ADHM44 | AGCGCTTGATGGCGTGRTGNGGNGT | Reverse | |
| ADHM45 | GACAACGTCGTCGTCTACGGNCCNTG GGG | Forward | |
| ADHM46 | GATGGTCGGCTGGTAGCCNACRAART CNA | Reverse | |
| ADHS1: | | | |

What is claimed is:

1. An isolated polypeptide that has the biological activity of an NAD- or NADP-dependent alcohol dehydrogenase and which comprises the sequence of SEQ ID NO:34.

2. The polypeptide of claim 1, wherein said polypeptide consists of the amino acid sequence of SEQ ID NO:34.

3. A process for producing an organic product, comprising reacting the polypeptide of claim 1 with a substrate of said polypeptide and, optionally, with a cofactor of said polypeptide.

4. The process of claim 3, wherein said polypeptide consists of the amino acid sequence of SEQ ID NO:34.

5. The process of claim 3, further comprising:
a) isolating the product of the reaction;
b) processing the product to give a medicament.

6. The process of claim 5, wherein said polypeptide consists of the amino acid sequence of SEQ ID NO:34.

7. The process of claim 3, wherein said organic product is an enantiomerically pure alcohol.

8. The process of claim 7, wherein said polypeptide consists of the amino acid sequence of SEQ ID NO:34.

9. A composition comprising the polypeptide of claim 1 and, in addition, at least one organic compound.

10. The composition of claim 9, wherein said polypeptide consists of the amino acid sequence of SEQ ID NO:34.

11. The composition of claim 9, wherein said organic compound is a carbonyl compound or an alcohol.

12. The composition of claim 11, wherein said polypeptide consists of the amino acid sequence of SEQ ID NO:34.

13. The composition of claim 9, further comprising NADH, NADPH, $NAD^+$ or $NADP^+$.

14. The composition of claim 13, wherein said polypeptide consists of the amino acid sequence of SEQ ID NO:34.

15. The composition of claim 13, wherein said the organic compound is a carbonyl compound or an alcohol.

16. The composition of claim 15, wherein said polypeptide consists of the amino acid sequence of SEQ ID NO:34.

17. The composition of claim 9, wherein said organic compound is an aldehyde, a ketone, a primary alcohol or a chiral secondary alcohol.

18. The composition of claim 17, wherein said polypeptide consists of the amino acid sequence of SEQ ID NO:34.

19. The composition of claim 9, wherein said organic compound is an asymmetrically substituted ketone.

20. The composition of claim 19, wherein said polypeptide consists of the amino acid sequence of SEQ ID NO:34.

* * * * *

SEQUENCE LISTING

<160> NUMBER OF SEQ ID NOS: 68

<210> SEQ ID NO 1
<211> LENGTH: 162
<212> TYPE: PRT
<213> ORGANISM: unknown
<220> FEATURE:
<223> OTHER INFORMATION: ZF0002326= Actinoplanes missouriensis;
ZF0003505= Streptomyces; ZF0050197= Pseudomonas oleovorans;
ZF0050294= Rhodococcus; ZF0050330= Bacillus; ZF0051303= Bacterium;
ZF0051337= Methylomonas; ZF0051321= Bacterium; ZF0050782=
Lactobacillus bulgaricus;
<220> FEATURE:
<223> OTHER INFORMATION: ZF0050544= Phyllobacterium rubiacearum;
ZF0002852= Rhodococcus; ZF0050310= Arthrobacter paraffineus;
ZF0002862= Streptomyces clavuligerus; ZF0050292= Bacterium;
ZF0002031= Streptomyces; ZF0002349= Streptomyces spectabilis;
ZF0002434= Streptomyces;
<220> FEATURE:
<223> OTHER INFORMATION: ZF0002437= Streptomyces; ZF0003712=
Micromonospora; ZF0003765= Streptomyces; ZF0051305= Bacterium;
ZF0003513= Actinomyces; ZF0050993= Kocuria; ZF0002018=
Streptomyces; ZF0003767= Actinomyces; ZF0002332= Streptomyces
diastatochromogenes; ZF0003768= Actinomyces; ZF0002379=
<220> FEATURE:
<223> OTHER INFORMATION: Streptomyces coelescens; ZF0002351= Nonomuraea
roseoviolacea; ZF0003769= Actinomyces;

<400> SEQUENCE: 1

Gly Pro Trp Gly Cys Gly Asn Cys Trp His Cys Ser Gln Gly Leu Glu
1               5                   10                  15

Asn Tyr Cys Ser Arg Ala Gln Glu Leu Gly Ile Asn Pro Pro Gly Leu
            20                  25                  30

Gly Ala Pro Gly Ala Leu Ala Glu Phe Met Ile Val Asp Ser Pro Arg
        35                  40                  45

His Leu Val Pro Ile Gly Asp Leu Asp Pro Val Lys Thr Val Pro Leu
    50                  55                  60

Thr Asp Ala Gly Leu Thr Pro Tyr His Ala Ile Lys Arg Ser Leu Pro
65                  70                  75                  80

Lys Leu Arg Gly Gly Ser Tyr Ala Val Val Ile Gly Thr Gly Gly Leu
                85                  90                  95

Gly His Val Ala Ile Gln Leu Leu Arg His Leu Ser Ala Ser Thr Val
            100                 105                 110

Ile Ala Leu Asp Val Ser Ala Asp Lys Leu Glu Leu Ala Thr Lys Val
        115                 120                 125

Gly Ala His Glu Val Val Leu Ser Asp Lys Asp Ala Ala Glu Asn Val
    130                 135                 140

Arg Lys Ile Thr Gly Ser Gln Gly Ala Ala Leu Val Leu Asp Phe Val
145                 150                 155                 160

Gly Tyr

<210> SEQ ID NO 2
<211> LENGTH: 128
<212> TYPE: PRT
<213> ORGANISM: unknown
<220> FEATURE:
<223> OTHER INFORMATION: ZF0002326= Actinoplanes missouriensis;
ZF0003505= Streptomyces; ZF0050197= Pseudomonas oleovorans;
ZF0050294= Rhodococcus; ZF0050330= Bacillus; ZF0051303= Bacterium;
ZF0051337= Methylomonas; ZF0051321= Bacterium; ZF0050782=
Lactobacillus bulgaricus;
<220> FEATURE:
<223> OTHER INFORMATION: ZF0050544= Phyllobacterium rubiacearum;
ZF0002852= Rhodococcus; ZF0050310= Arthrobacter paraffineus;

```
        ZF0002862= Streptomyces clavuligerus; ZF0050292= Bacterium;
        ZF0002031= Streptomyces; ZF0002349= Streptomyces spectabilis;
        ZF0002434= Streptomyces;
<220> FEATURE:
<223> OTHER INFORMATION: ZF0002437= Streptomyces; ZF0003712=
        Micromonospora; ZF0003765= Streptomyces; ZF0051305= Bacterium;
        ZF0003513= Actinomyces; ZF0050993= Kocuria; ZF0002018=
        Streptomyces; ZF0003767= Actinomyces; ZF0002332= Streptomyces
        diastatochromogenes; ZF0003768= Actinomyces;
<220> FEATURE:
<223> OTHER INFORMATION: ZF0002379= Streptomyces coelescens; ZF0002351=
        Nonomuraea roseoviolacea; ZF0003769= Actinomyces;

<400> SEQUENCE: 2

Gly Pro Trp Gly Cys Gly Asn Cys Trp His Cys Ser Gln Gly Leu Glu
1               5                   10                  15

Asn Tyr Cys Ser Arg Ala Gln Glu Leu Gly Ile Asn Pro Pro Gly Leu
                20                  25                  30

Gly Ala Pro Gly Ala Leu Ala Glu Phe Met Ile Val Asp Ser Pro Arg
            35                  40                  45

His Leu Val Pro Ile Gly Asp Leu Asp Pro Val Lys Thr Val Pro Leu
        50                  55                  60

Thr Asp Ala Gly Leu Thr Pro Tyr His Ala Ile Lys Arg Ser Leu Pro
65                  70                  75                  80

Lys Leu Arg Gly Gly Ser Tyr Ala Val Val Ile Gly Thr Gly Gly Leu
                85                  90                  95

Gly His Val Thr Ile Gln Leu Leu Arg His Leu Ser Ala Ala Thr Val
            100                 105                 110

Ile Ala Leu Asp Val Ser Ala Asp Lys Leu Glu Leu Ala Thr Lys Val
        115                 120                 125

<210> SEQ ID NO 3
<211> LENGTH: 162
<212> TYPE: PRT
<213> ORGANISM: unknown
<220> FEATURE:
<223> OTHER INFORMATION: ZF0050286= Corynebacterium hoagii

<400> SEQUENCE: 3

Gly Pro Trp Gly Cys Gly Arg Cys Trp His Cys Ala Gln Gly Leu Glu
1               5                   10                  15

Asn Tyr Cys Ser Arg Ala Arg Glu Leu Gly Ile Ala Pro Pro Gly Leu
                20                  25                  30

Gly Ala Pro Gly Ala Ile Ala Glu Tyr Met Ile Val Asp Ser Pro Arg
            35                  40                  45

His Leu Val Pro Ile Gly Asp Leu Asp Pro Val Thr Thr Val Pro Leu
        50                  55                  60

Thr Asp Ala Gly Leu Thr Pro Tyr His Ala Ile Lys Arg Ser Leu Gly
65                  70                  75                  80

Lys Leu Arg Ala Gly Ser Tyr Ala Val Val Ile Gly Thr Gly Gly Leu
                85                  90                  95

Gly His Val Gly Ile Gln Leu Leu Arg His Leu Ser Pro Ala Arg Ile
            100                 105                 110

Ile Ala Leu Asp Val Asn Asp Glu Lys Leu Ala Phe Ala Arg Glu Val
        115                 120                 125

Gly Ala His Glu Thr Val Leu Ser Asn Ala Asp Ala Ala Ala Asn Val
            130                 135                 140

Arg Lys Ile Thr Gly Ser Ala Gly Ala Ala Leu Val Leu Asp Phe Val
145                 150                 155                 160
```

```
Gly Tyr

<210> SEQ ID NO 4
<211> LENGTH: 161
<212> TYPE: PRT
<213> ORGANISM: unknown
<220> FEATURE:
<223> OTHER INFORMATION: ZF0050310= Arthrobacter paraffineus

<400> SEQUENCE: 4

Gly Pro Trp Gly Cys Gly Ser Cys Trp His Cys Ser Gln Gly Leu Glu
1               5                   10                  15

Asn Tyr Cys Ser Arg Ala Lys Glu Leu Gly Ile Asn Pro Pro Gly Leu
            20                  25                  30

Gly Ala Pro Gly Ala Leu Ala Glu Phe Met Ile Val Asp Ser Pro Arg
        35                  40                  45

His Leu Val Pro Ile Gly Asp Leu Asp Pro Val Lys Thr Val Pro Leu
    50                  55                  60

Thr Asp Ala Gly Leu Thr Pro Tyr His Ala Ile Lys Arg Ser Leu Pro
65                  70                  75                  80

Lys Leu Arg Gly Gly Ala Tyr Ala Val Val Ile Gly Thr Gly Gly Leu
                85                  90                  95

Gly His Val Ala Ile Gln Leu Leu Arg His Leu Ser Ala Ala Thr Val
            100                 105                 110

Ile Ala Leu Asp Val Ser Ala Asp Lys Leu Val Leu Ala Thr Lys Val
        115                 120                 125

Gly Ala His Glu Val Val Leu Ser Asp Lys Asp Ala Ala Glu Asn Val
    130                 135                 140

Arg Arg Ile Thr Gly Ser Gln Gly Ala Ala Leu Val Leu Asp Phe Val
145                 150                 155                 160

Gly

<210> SEQ ID NO 5
<211> LENGTH: 70
<212> TYPE: PRT
<213> ORGANISM: unknown
<220> FEATURE:
<223> OTHER INFORMATION: ZF0004210= Actinomyces; ZF0004212= Actinomyces;
      ZF0004211= Actinomyces; ZF0003860= Actinomyces; ZF0004218=
      Actinomyces; ZF0003868= Actinomadura; ZF0004213= Actinomyces;
      ZF0003876= Actinomyces; ZF0003866= Actinomyces; ZF0003864=
      Actinomyces;
<220> FEATURE:
<223> OTHER INFORMATION: ZF0003862= Actinomadura; ZF0003869=
      Actinomyces; ZF0003867= Actinomadura; ZF0004216= Actinomyces;
      ZF0004235= Actinomyces; ZF0004209= Actinomadura; ZF0004214=
      Actinomyces; ZF0003871= Actinomyces; ZF0004063= Actinomadura;
      ZF0004052= Actinomadura;
<220> FEATURE:
<223> OTHER INFORMATION: ZF0006405= Streptomyces; ZF0003865=
      Actinomadura; ZF0004047= Actinomadura; ZF0004070= Actinomyces;
      ZF0004085= Actinomyces; ZF0004217= Actinomyces; ZF0004089=
      Actinomyces; ZF0004090= Actinomadura; ZF0006138= Streptomyces;
      ZF0004236= Actinomadura;
<220> FEATURE:
<223> OTHER INFORMATION: ZF0051203= Bacterium;

<400> SEQUENCE: 5

Gly Pro Trp Gly Cys Gly Thr Cys Val Lys Cys Ala Glu Gly Lys Glu
1               5                   10                  15

Asn Tyr Cys Leu Arg Ala Lys Glu Leu Gly Ile Ala Pro Pro Gly Leu
            20                  25                  30

Gly Ser Pro Gly Ala Met Ala Glu Tyr Met Ile Val Asp Asp Pro Arg
```

-continued

```
                35                  40                  45

His Leu Val Pro Leu Gly Gly Leu Asp Pro Val Gln Ala Val Pro Leu
    50                  55                  60

Thr Asp Ala Gly Leu Thr
65                  70

<210> SEQ ID NO 6
<211> LENGTH: 94
<212> TYPE: PRT
<213> ORGANISM: unknown
<220> FEATURE:
<223> OTHER INFORMATION: ZF0002326= Actinoplanes missouriensis;
      ZF0003505= Streptomyces; ZF0051321= Bacterium; ZF0050782=
      Lactobacillus bulgaricus; ZF0050544= Phyllobacterium rubiacearum;
      ZF0002031= Streptomyces; ZF0002349= Streptomyces spectabilis;
      ZF0002434= Streptomyces; ZF0050993= Kocuria;
<220> FEATURE:
<223> OTHER INFORMATION: ZF0002018= Streptomyces; ZF0003767=
      Actinomyces; ZF0003764= Streptomyces; ZF0002331= Actinoplanes
      philippinensis; ZF0002441= Streptomyces; ZF0051307= Bacterium;
      ZF0051301= Bacterium; ZF0051240= Bacterium; ZF0002333=
      Rhodococcus erythropolis;
<220> FEATURE:
<223> OTHER INFORMATION: ZF0003713= Micromonospora; ZF0004980=
      Streptomyces; ZF0004821= Actinomyces; ZF0002359= Actinoplanes
      ianthinogenes; ZF0002396= Actinoplanes; ZF0003781= Actinomyces;
      ZF0003512= Actinomyces; ZF0006093= Streptomyces; ZF0006103=
      Streptomyces;
<220> FEATURE:
<223> OTHER INFORMATION: ZF0006087= Streptomyces; ZF0050446= Bacterium;
      ZF0050445= Bacterium; ZF0006086= Streptomyces; ZF0002322=
      Rhodococcus; ZF0003538= Actinomyces; ZF0003535= Actinomyces;

<400> SEQUENCE: 6

Cys His Thr Asp His His Ile Val Thr Gly Ala Thr Pro Met Pro Ser
1               5                   10                  15

Phe Pro Val Met Gly Gly His Glu Gly Ser Gly Val Ile Thr Lys Leu
                20                  25                  30

Gly Pro Glu Val Lys Gly Leu Glu Val Gly Asp His Val Leu Ser
            35                  40                  45

Phe Ile Pro Ala Cys Gly Thr Cys Pro Ala Cys Ser Ala Gly His Gln
    50                  55                  60

Asn Leu Cys Asp Leu Gly Met Gly Leu Leu Ser Gly Gln Ala Ile Ser
65                  70                  75                  80

Asp Gly Thr Tyr Arg Ile Gln Ala Arg Gly Glu Asn Val Ile
                85                  90

<210> SEQ ID NO 7
<211> LENGTH: 92
<212> TYPE: PRT
<213> ORGANISM: unknown
<220> FEATURE:
<223> OTHER INFORMATION: ZF0002326= Actinoplanes missouriensis;
      ZF0003505= Streptomyces; ZF0051321= Bacterium; ZF0050782=
      Lactobacillus bulgaricus; ZF0050544= Phyllobacterium rubiacearum;
      ZF0002031= Streptomyces; ZF0002349= Streptomyces spectabilis;
      ZF0002434= Streptomyces; ZF0050993= Kocuria;
<220> FEATURE:
<223> OTHER INFORMATION: ZF0002018= Streptomyces; ZF0003767=
      Actinomyces; ZF0003764= Streptomyces; ZF0002331= Actinoplanes
      philippinensis; ZF0002441= Streptomyces; ZF0051307= Bacterium;
      ZF0051301= Bacterium; ZF0051240= Bacterium; ZF0002333=
      Rhodococcus erythropolis;
<220> FEATURE:
<223> OTHER INFORMATION: ZF0003713= Micromonospora; ZF0004980=
      Streptomyces; ZF0004821= Actinomyces; ZF0002359= Actinoplanes
      ianthinogenes; ZF0002396= Actinoplanes; ZF0003781= Actinomyces;
      ZF0003512= Actinomyces; ZF0006093= Streptomyces; ZF0006103=
      Streptomyces;
```

```
<220> FEATURE:
<223> OTHER INFORMATION: ZF0006087= Streptomyces; ZF0050446= Bacterium;
      ZF0050445= Bacterium; ZF0006086= Streptomyces; ZF0002322=
      Rhodococcus; ZF0003538= Actinomyces; ZF0003535= Actinomyces;

<400> SEQUENCE: 7

Cys His Thr Asp Asp His Ala Val Thr Gly Asp Leu Ala Val Pro Leu
1               5                   10                  15

Pro Val Ile Gly Gly His Glu Gly Ala Gly Ile Val Glu Lys Val Gly
            20                  25                  30

Pro Gly Val Arg Asp Val Glu Val Gly Asp His Val Val Leu Ser Phe
        35                  40                  45

Ile Pro Ser Cys Gly Arg Cys Arg Trp Cys Ala Val Gly Gln Ser Asn
    50                  55                  60

Leu Cys Asp Leu Gly Ala Ile Leu Met Ala Gly Ala Gln Val Asp Gly
65                  70                  75                  80

Thr Tyr Arg Ala Thr Ala Arg Gly His Asp Val Gly
                85                  90

<210> SEQ ID NO 8
<211> LENGTH: 92
<212> TYPE: PRT
<213> ORGANISM: unknown
<220> FEATURE:
<223> OTHER INFORMATION: ZF0002326= Actinoplanes missouriensis;
      ZF0003505= Streptomyces; ZF0051321= Bacterium; ZF0050782=
      Lactobacillus bulgaricus; ZF0050544= Phyllobacterium rubiacearum;
      ZF0002031= Streptomyces; ZF0002349= Streptomyces spectabilis;
      ZF0002434= Streptomyces; ZF0050993= Kocuria;
<220> FEATURE:
<223> OTHER INFORMATION: ZF0002018= Streptomyces; ZF0003767=
      Actinomyces; ZF0003764= Streptomyces; ZF0002331= Actinoplanes
      philippinensis; ZF0002441= Streptomyces; ZF0051307= Bacterium;
      ZF0051301= Bacterium; ZF0051240= Bacterium; ZF0002333= Rhodococcus
      erythropolis;
<220> FEATURE:
<223> OTHER INFORMATION: ZF0003713= Micromonospora; ZF0004980=
      Streptomyces; ZF0004821= Actinomyces; ZF0002359= Actinoplanes
      ianthinogenes; ZF0002396= Actinoplanes; ZF0003781= Actinomyces;
      ZF0003512= Actinomyces; ZF0006093= Streptomyces; ZF0006103=
      Streptomyces;
<220> FEATURE:
<223> OTHER INFORMATION: ZF0006087= Streptomyces; ZF0050446= Bacterium;
      ZF0050445= Bacterium; ZF0006086= Streptomyces; ZF0002322=
      Rhodococcus; ZF0003538= Actinomyces; ZF0003535= Actinomyces;

<400> SEQUENCE: 8

Cys His Thr Asp Asp His Ala Val Thr Gly Asp Leu Ala Val Pro Leu
1               5                   10                  15

Pro Val Ile Gly Gly His Glu Gly Ala Gly Ile Val Glu Lys Val Gly
            20                  25                  30

Pro Gly Val Arg Asp Val Glu Val Gly Asp His Val Val Leu Ser Phe
        35                  40                  45

Ile Pro Ser Cys Gly Arg Cys Arg Trp Cys Ala Val Gly Gln Ser Asn
    50                  55                  60

Leu Cys Asp Leu Gly Ala Ile Leu Met Ala Gly Ala Gln Val Asp Gly
65                  70                  75                  80

Thr Tyr Arg Ala Thr Ala Arg Gly His Asp Val Gly
                85                  90

<210> SEQ ID NO 9
<211> LENGTH: 92
<212> TYPE: PRT
<213> ORGANISM: unknown
<220> FEATURE:
```

-continued

<223> OTHER INFORMATION: ZF0002326= Actinoplanes missouriensis;
    ZF0003505= Streptomyces; ZF0051321= Bacterium; ZF0050782=
    Lactobacillus bulgaricus; ZF0050544= Phyllobacterium rubiacearum;
    ZF0002031= Streptomyces; ZF0002349= Streptomyces spectabilis;
    ZF0002434= Streptomyces; ZF0050993= Kocuria;
<220> FEATURE:
<223> OTHER INFORMATION: ZF0002018= Streptomyces; ZF0003767=
    Actinomyces; ZF0003764= Streptomyces; ZF0002331= Actinoplanes
    philippinensis; ZF0002441= Streptomyces; ZF0051307= Bacterium;
    ZF0051301= Bacterium; ZF0051240= Bacterium; ZF0002333= Rhodococcus
    erythropolis;
<220> FEATURE:
<223> OTHER INFORMATION: ZF0003713= Micromonospora; ZF0004980=
    Streptomyces; ZF0004821= Actinomyces; ZF0002359= Actinoplanes
    ianthinogenes; ZF0002396= Actinoplanes; ZF0003781= Actinomyces;
    ZF0003512= Actinomyces; ZF0006093= Streptomyces; ZF0006103=
    Streptomyces;
<220> FEATURE:
<223> OTHER INFORMATION: ZF0006087= Streptomyces; ZF0050446= Bacterium;
    ZF0050445= Bacterium; ZF0006086= Streptomyces; ZF0002322=
    Rhodococcus; ZF0003538= Actinomyces; ZF0003535= Actinomyces;

<400> SEQUENCE: 9

Cys His Thr Asp Asp His Ala Val Thr Gly Asp Leu Ala Val Pro Leu
1               5                   10                  15

Pro Val Ile Gly Gly His Glu Gly Ala Gly Ile Val Glu Lys Val Gly
            20                  25                  30

Pro Gly Val Arg Asp Val Glu Val Gly Asp His Val Val Leu Ser Phe
        35                  40                  45

Ile Pro Ser Cys Gly Arg Cys Arg Trp Cys Ala Val Gly Gln Ser Asn
    50                  55                  60

Leu Cys Asp Leu Gly Ala Ile Leu Met Ala Gly Ala Gln Val Asp Gly
65                  70                  75                  80

Thr Tyr Arg Ala Thr Ala Arg Gly His Asp Val Gly
                85                  90

<210> SEQ ID NO 10
<211> LENGTH: 92
<212> TYPE: PRT
<213> ORGANISM: unknown
<220> FEATURE:
<223> OTHER INFORMATION: ZF0002326= Actinoplanes missouriensis;
    ZF0003505= Streptomyces; ZF0051321= Bacterium; ZF0050782=
    Lactobacillus bulgaricus; ZF0050544= Phyllobacterium rubiacearum;
    ZF0002031= Streptomyces; ZF0002349= Streptomyces spectabilis;
    ZF0002434= Streptomyces; ZF0050993= Kocuria;
<220> FEATURE:
<223> OTHER INFORMATION: ZF0002018= Streptomyces; ZF0003767=
    Actinomyces; ZF0003764= Streptomyces; ZF0002331= Actinoplanes
    philippinensis; ZF0002441= Streptomyces; ZF0051307= Bacterium;
    ZF0051301= Bacterium; ZF0051240= Bacterium; ZF0002333= Rhodococcus
    erythropolis;
<220> FEATURE:
<223> OTHER INFORMATION: ZF0003713= Micromonospora; ZF0004980=
    Streptomyces; ZF0004821= Actinomyces; ZF0002359= Actinoplanes
    ianthinogenes; ZF0002396= Actinoplanes; ZF0003781= Actinomyces;
    ZF0003512= Actinomyces; ZF0006093= Streptomyces; ZF0006103=
    Streptomyces;
<220> FEATURE:
<223> OTHER INFORMATION: ZF0006087= Streptomyces; ZF0050446= Bacterium;
    ZF0050445= Bacterium; ZF0006086= Streptomyces; ZF0002322=
    Rhodococcus; ZF0003538= Actinomyces; ZF0003535= Actinomyces;

<400> SEQUENCE: 10

Cys His Thr Asp Asp His Ala Val Thr Gly Asp Leu Ala Val Pro Leu
1               5                   10                  15

Pro Val Ile Gly Gly His Glu Gly Ala Gly Ile Val Glu Lys Val Gly
            20                  25                  30

Pro Gly Val Arg Asp Val Glu Val Gly Asp His Val Val Leu Ser Phe

```
                    35                  40                  45

Ile Pro Ser Cys Gly Arg Cys Arg Trp Cys Ala Val Gly Gln Ser Asn
 50                  55                  60

Leu Cys Asp Leu Gly Ala Ile Leu Met Ala Gly Ala Arg Val Asp Gly
65                  70                  75                  80

Thr Tyr Arg Ala Thr Ala Arg Gly His Asp Val Gly
                85                  90

<210> SEQ ID NO 11
<211> LENGTH: 92
<212> TYPE: PRT
<213> ORGANISM: unknown
<220> FEATURE:
<223> OTHER INFORMATION: ZF0002326= Actinoplanes missouriensis;
      ZF0003505= Streptomyces; ZF0051321= Bacterium; ZF0050782=
      Lactobacillus bulgaricus; ZF0050544= Phyllobacterium rubiacearum;
      ZF0002031= Streptomyces; ZF0002349= Streptomyces spectabilis;
      ZF0002434= Streptomyces; ZF0050993= Kocuria;
<220> FEATURE:
<223> OTHER INFORMATION: ZF0002018= Streptomyces; ZF0003767=
      Actinomyces; ZF0003764= Streptomyces; ZF0002331= Actinoplanes
      philippinensis; ZF0002441= Streptomyces; ZF0051307= Bacterium;
      ZF0051301= Bacterium; ZF0051240= Bacterium; ZF0002333= Rhodococcus
      erythropolis;
<220> FEATURE:
<223> OTHER INFORMATION: ZF0003713= Micromonospora; ZF0004980=
      Streptomyces; ZF0004821= Actinomyces; ZF0002359= Actinoplanes
      ianthinogenes; ZF0002396= Actinoplanes; ZF0003781= Actinomyces;
      ZF0003512= Actinomyces; ZF0006093= Streptomyces; ZF0006103=
      Streptomyces;
<220> FEATURE:
<223> OTHER INFORMATION: ZF0006087= Streptomyces; ZF0050446= Bacterium;
      ZF0050445= Bacterium; ZF0006086= Streptomyces; ZF0002322=
      Rhodococcus; ZF0003538= Actinomyces; ZF0003535= Actinomyces;

<400> SEQUENCE: 11

Cys His Thr Asp Asp His Ala Val Thr Gly Asp Leu Ala Val Pro Leu
1               5                  10                  15

Pro Val Ile Gly Gly His Glu Gly Ala Gly Ile Val Glu Lys Val Gly
                20                  25                  30

Pro Gly Val Arg Asp Val Glu Val Gly Asp His Val Val Leu Ser Phe
            35                  40                  45

Ile Pro Ser Cys Gly Arg Cys Arg Trp Cys Ala Val Gly Gln Ser Asn
 50                  55                  60

Leu Cys Asp Leu Gly Ala Ile Leu Met Ala Gly Ala Gln Val Asp Gly
65                  70                  75                  80

Thr Tyr Arg Ala Thr Ala Arg Gly His Asp Val Gly
                85                  90

<210> SEQ ID NO 12
<211> LENGTH: 93
<212> TYPE: PRT
<213> ORGANISM: unknown
<220> FEATURE:
<223> OTHER INFORMATION: ZF0050310= Arthrobacter paraffineus

<400> SEQUENCE: 12

Cys His Thr Asp Leu Phe Thr Lys Ser Val Leu Pro Glu Arg Leu Gly
1               5                  10                  15

Pro Cys Val Phe Gly His Glu Gly Ala Gly Val Val Glu Ala Val Gly
                20                  25                  30

Ser Ser Ile Asp Ser Ile Ala Pro Gly Asp His Val Leu Leu Ser Tyr
            35                  40                  45

Arg Ser Cys Gly Val Cys Arg Gln Cys Leu Ser Gly His Arg Ala Tyr
```

```
                50              55              60
Cys Glu Ser Ser His Gly Leu Asn Ser Ser Gly Ala Arg Thr Asp Gly
 65                  70                  75                  80

Ser Thr Pro Val Arg Arg Ser Gly Thr Pro Ile Arg Ser
                85                  90
```

<210> SEQ ID NO 13
<211> LENGTH: 93
<212> TYPE: PRT
<213> ORGANISM: unknown
<220> FEATURE:
<223> OTHER INFORMATION: ZF0002333=Rhodoccocus erythropolis

<400> SEQUENCE: 13

```
Cys His Thr Asp Leu Phe Thr Lys Thr Val Leu Pro Glu Lys Leu Gly
  1               5                  10                  15

Pro Cys Val Phe Gly His Glu Gly Ala Gly Val Val Gln Ala Val Gly
                 20                  25                  30

Ser Ser Ile Asp Asn Ile Ala Ala Gly Asp His Val Leu Leu Ser Tyr
             35                  40                  45

Arg Ser Cys Gly Val Cys Arg Gln Cys Leu Ser Asp His Arg Ala Tyr
     50                  55                  60

Cys Glu Ser Ser His Gly Leu Asn Ser Ser Gly Ala Arg Thr Asp Gly
 65                  70                  75                  80

Ser Thr Pro Val Arg Arg Asn Gly Thr Pro Ile Arg Ser
                85                  90
```

<210> SEQ ID NO 14
<211> LENGTH: 120
<212> TYPE: PRT
<213> ORGANISM: unknown
<220> FEATURE:
<223> OTHER INFORMATION: ZF0051303= Bacterium; ZF0051337= Methylomonas;
      ZF0002862= Streptomyces clavuligerus; ZF0050292= Bacterium;
      ZF0051305= Bacterium; ZF0003513= Actinomyces; ZF0002351=
      Nonomuraea roseoviolacea; ZF0003769= Actinomyces; ZF0002017=
      Streptomyces; ZF0051306= Bacterium;
<220> FEATURE:
<223> OTHER INFORMATION: ZF0002016= Streptomyces; ZF0003504=
      Actinomyces; ZF0006073= Streptomyces; ZF0003770= Actinomyces;
      ZF0002352= Actinoplanes italicus; ZF0002378= Streptomyces
      aureomonopodiales; ZF0006089= Streptomyces; ZF0006106=
      Streptomyces; ZF0051325= Bacterium;
<220> FEATURE:
<223> OTHER INFORMATION: ZF0006108= Streptomyces; ZF0002440=
      Streptomyces; ZF0051302= Bacterium; ZF0003532= Actinomyces;
      ZF0003548= Nocardiaform;

<400> SEQUENCE: 14

```
Cys Gly Thr Asp Arg Glu Ile Ala Ser Gly Ile Tyr Gly Trp Ala Pro
  1               5                  10                  15

Pro Gly Arg Glu His Leu Val Leu Gly His Glu Ser Leu Gly Arg Val
                 20                  25                  30

Arg Thr Ala Pro Asp Gly Ser Gly Phe Ala Ala Gly Asp Leu Val Val
             35                  40                  45

Gly Ile Val Arg Arg Pro Asp Pro Val Pro Cys Gly Ala Cys Ala His
     50                  55                  60

Gly Glu Phe Asp Met Cys Arg Asn Gly Glu Tyr Val Glu Arg Gly Ile
 65                  70                  75                  80

Lys Gln Ile Asp Gly Tyr Gly Ser Thr Ser Trp Val Val Asp Ala Asp
                85                  90                  95

Tyr Thr Val Lys Leu Asp Pro Ala Leu Thr Glu Val Gly Val Leu Met
```

-continued

```
                100                 105                 110
Glu Pro Thr Thr Val Leu Gly Gln
        115                 120

<210> SEQ ID NO 15
<211> LENGTH: 140
<212> TYPE: PRT
<213> ORGANISM: unknown
<220> FEATURE:
<223> OTHER INFORMATION: ZF0051303= Bacterium; ZF0051337= Methylomonas;
      ZF0002862= Streptomyces clavuligerus; ZF0050292= Bacterium;
      ZF0051305= Bacterium; ZF0003513= Actinomyces; ZF0002351=
      Nonomuraea roseoviolacea; ZF0003769= Actinomyces; ZF0002017=
      Streptomyces; ZF0051306= Bacterium;
<220> FEATURE:
<223> OTHER INFORMATION: ZF0002016= Streptomyces; ZF0003504=
      Actinomyces; ZF0006073= Streptomyces; ZF0003770= Actinomyces;
      ZF0002352= Actinoplanes italicus; ZF0002378= Streptomyces
      aureomonopodiales; ZF0006089= Streptomyces; ZF0006106=
      Streptomyces; ZF0051325= Bacterium;
<220> FEATURE:
<223> OTHER INFORMATION: ZF0006108= Streptomyces; ZF0002440=
      Streptomyces; ZF0051302= Bacterium; ZF0003532= Actinomyces;
      ZF0003548= Nocardiaform;

<400> SEQUENCE: 15

Cys Gly Thr Asp Leu His Ile Arg Ser Trp Asp Gly Trp Ala Gln Lys
1               5                   10                  15

Thr Ile Ala Thr Pro Leu Thr Leu Gly His Glu Phe Val Gly Glu Val
            20                  25                  30

Val Glu Thr Gly Arg Asp Val Thr Asp Ile Gln Val Gly Asp Leu Val
        35                  40                  45

Ser Gly Glu Gly His Leu Val Cys Gly Lys Cys Arg Asn Cys Leu Ala
    50                  55                  60

Gly Arg Arg His Leu Cys Arg Ala Thr Val Gly Leu Gly Val Gly Arg
65                  70                  75                  80

Asp Gly Ala Phe Ala Glu Tyr Val Val Leu Pro Ala Ser Asn Val Trp
                85                  90                  95

Val His Arg Val Pro Val Asp Leu Asp Val Ala Ala Ile Phe Asp Pro
            100                 105                 110

Phe Gly Asn Ala Val His Thr Ala Leu Ser Phe Pro Leu Val Gly Glu
        115                 120                 125

Asp Val Leu Val Thr Gly Ala Gly Thr Ile Gly Ile
    130                 135                 140

<210> SEQ ID NO 16
<211> LENGTH: 138
<212> TYPE: PRT
<213> ORGANISM: unknown
<220> FEATURE:
<223> OTHER INFORMATION: ZF0050197= Pseudomonas oleovorans; ZF0050294=
      Rhodococcus; ZF0050330= Bacillus, ZF0002852= Rhodococcus;
      ZF0050310= Arthrobacter paraffineus; ZF0002437= Streptomyces;
      ZF0003712= Micromonospora; ZF0003765= Streptomyces; ZF0002332=
      Streptomyces diatsatochromogenes;
<220> FEATURE:
<223> OTHER INFORMATION: ZF0003768= Actinomyces; ZF0002379= Streptomyces
      coelescens; ZF0002443= Streptomyces; ZF0002442= Streptomyces;
      ZF0002436= Streptomyces; ZF0050994= Bacterium; ZF0050992=
      Bacterium; ZF0050442= Bacterium; ZF0002049= Streptomyces;
      ZF0006069= Streptomyces;
<220> FEATURE:
<223> OTHER INFORMATION: ZF0006075= Streptomyces; ZF0004724=
      Nocardiaform; ZF0002392= Actinoplanes nipponensis; ZF0002356=
      Actinoplanes brasiliensis; ZF0003501= Actinomyces; ZF0051322=
      Bacterium; ZF0006078= Streptomyces; ZF0006092= Streptomyces;
      ZF0006090= Streptomyces;
```

-continued

```
<220> FEATURE:
<223> OTHER INFORMATION: ZF0006084= Streptomyces; ZF0006068=
      Streptomyces; ZF0050284= Rhodococcus; ZF0050028= Agrobacterium
      tumefaciens; ZF0003540= Actinomyces; ZF0003528= Actinomyces;
      ZF0003529= Actinomyces;

<400> SEQUENCE: 16

Gly Leu Thr Ile Gly His Glu Pro Val Gly Val Ile Glu Lys Leu Gly
1               5                   10                  15

Ser Ala Val Thr Gly Tyr Arg Glu Gly Gln Arg Val Ile Ala Gly Ala
            20                  25                  30

Ile Cys Pro Asn Phe Asn Ser Tyr Ala Ala Gln Asp Gly Ala Pro Ser
        35                  40                  45

Gln Asp Gly Ser Tyr Leu Val Ala Ser Gly Ala Cys Gly Cys His Gly
    50                  55                  60

Tyr Arg Ala Thr Ala Gly Trp Arg Phe Gly Asn Ile Ile Asp Gly Ala
65                  70                  75                  80

Gln Ala Glu Tyr Leu Leu Val Pro Asp Ala Gln Gly Asn Leu Ala Pro
                85                  90                  95

Val Pro Asp Asn Leu Ser Asp Glu Gln Val Leu Met Cys Pro Asp Ile
            100                 105                 110

Met Ser Thr Gly Phe Lys Gly Ala Glu Asn Ala His Ile Arg Ile Gly
        115                 120                 125

Asp Thr Val Ala Val Phe Ala Gln Gly Pro
    130                 135

<210> SEQ ID NO 17
<211> LENGTH: 144
<212> TYPE: PRT
<213> ORGANISM: unknown
<220> FEATURE:
<223> OTHER INFORMATION: ZF0050197= Pseudomonas oleovorans; ZF0050294=
      Rhodococcus; ZF0050330= Bacillus, ZF0002852= Rhodococcus;
      ZF0050310= Arthrobacter paraffineus; ZF0002437= Streptomyces;
      ZF0003712= Micromonospora; ZF0003765= Streptomyces; ZF0002332=
      Streptomyces diatsatochromogenes;
<220> FEATURE:
<223> OTHER INFORMATION: ZF0003768= Actinomyces; ZF0002379= Streptomyces
      coelescens; ZF0002443= Streptomyces; ZF0002442= Streptomyces;
      ZF0002436= Streptomyces; ZF0050994= Bacterium; ZF0050992=
      Bacterium; ZF0050442= Bacterium; ZF0002049= Streptomyces;
      ZF0006069= Streptomyces;
<220> FEATURE:
<223> OTHER INFORMATION: ZF0006075= Streptomyces; ZF0004724=
      Nocardiaform; ZF0002392= Actinoplanes nipponensis; ZF0002356=
      Actinoplanes brasiliensis; ZF0003501= Actinomyces; ZF0051322=
      Bacterium; ZF0006078= Streptomyces; ZF0006092= Streptomyces;
      ZF0006090= Streptomyces;
<220> FEATURE:
<223> OTHER INFORMATION: ZF0006084= Streptomyces; ZF0006068=
      Streptomyces; ZF0050284= Rhodococcus; ZF0050028= Agrobacterium
      tumefaciens; ZF0003540= Actinomyces; ZF0003528= Actinomyces;
      ZF0003529= Actinomyces;

<400> SEQUENCE: 17

Cys Gly Thr Asp Leu His Ile Leu Gly Gly Asp Val Pro Glu Val Thr
1               5                   10                  15

Asp Gly Arg Ile Leu Gly His Glu Ala Val Gly Thr Val Glu Val
            20                  25                  30

Gly Asp Gly Val Gln Thr Leu Ala Pro Gly Asp Arg Val Leu Val Ser
        35                  40                  45

Cys Val Thr Ala Cys Gly Thr Cys Arg Phe Cys Arg Glu Ser Arg Tyr
    50                  55                  60

Gly Gln Cys Leu Gly Gly Gly Gly Trp Ile Leu Gly His Leu Ile Asp
```

```
                65                  70                  75                  80
Gly Thr Gln Ala Glu Leu Val Arg Val Pro Tyr Ala Asp Asn Ser Thr
                    85                  90                  95
His Arg Ile Pro Asp Gly Val Ser Asp Glu Gln Met Leu Met Leu Ala
                100                 105                 110
Asp Ile Leu Pro Thr Ser Tyr Glu Val Gly Val Leu Asn Gly Cys Leu
            115                 120                 125
Arg Pro Ala Asp Val Val Ile Ile Gly Ala Asp Asp Arg Pro Leu
        130                 135                 140

<210> SEQ ID NO 18
<211> LENGTH: 73
<212> TYPE: PRT
<213> ORGANISM: unknown
<220> FEATURE:
<223> OTHER INFORMATION: ZF0050310= Arthrobacter paraffineus

<400> SEQUENCE: 18

Val Asp Val Val Asp Asn Ala Gly Phe Gly Thr His Gly Ala Phe
1               5                   10                  15
Val Asp Glu Asp His Glu Arg Val Thr Ser Glu Ile Gln Leu Asn Ile
                20                  25                  30
Ala Thr Leu Val Glu Leu Thr His Thr Phe Pro Pro Asp Leu Leu Thr
            35                  40                  45
Gly Arg Gly Ala Leu Val Asn Ile Ala Ser Thr Ala Ser Phe Gln Pro
        50                  55                  60
Thr Pro Gly Met Ala Val Tyr Cys Ala
65                  70

<210> SEQ ID NO 19
<211> LENGTH: 75
<212> TYPE: PRT
<213> ORGANISM: unknown
<220> FEATURE:
<223> OTHER INFORMATION: ZF0050310= Arthrobacter paraffineus

<400> SEQUENCE: 19

Val Asp Val Val His Asn Ala Gly Phe Gly Thr His Gly Ala Phe
1               5                   10                  15
Val Asp Glu Asp Leu Glu Arg Val Thr Ser Glu Ile Gln Leu Asn Ile
                20                  25                  30
Ala Thr Leu Val Glu Leu Thr His Thr Phe Leu Pro Asp Leu Leu Thr
            35                  40                  45
Gly Arg Gly Ala Leu Val Asn Ile Ala Ser Thr Ala Ser Phe Gln Pro
        50                  55                  60
Thr Pro Gly Met Ala Val Tyr Cys Ala Thr Lys
65                  70                  75

<210> SEQ ID NO 20
<211> LENGTH: 79
<212> TYPE: PRT
<213> ORGANISM: unknown
<220> FEATURE:
<223> OTHER INFORMATION: ZF0003535= Actinomyces

<400> SEQUENCE: 20

Arg Val Asp Val Val His Asn Ala Ala Ile Thr Gln Lys Ala Thr
1               5                   10                  15
Phe Arg Asp Ile Thr Pro Ala Asp Phe Glu Arg Ile Leu Arg Val Asn
                20                  25                  30
```

```
Leu Thr Gly Val Phe Asn Leu Ser Gln Ala Val Ile Pro Leu Met Ile
        35                  40                  45

Gln Arg Gly Gly Gly Ser Ile Val Ser Ile Ser Ser Leu Ser Ala Gln
 50                  55                  60

Asn Gly Gly Gly Ile Phe Gly Gly Ala His Tyr Cys Ala Thr Lys
 65                  70                  75

<210> SEQ ID NO 21
<211> LENGTH: 76
<212> TYPE: PRT
<213> ORGANISM: unknown
<220> FEATURE:
<223> OTHER INFORMATION: ZF0003535= Actinomyces

<400> SEQUENCE: 21

Val Asp Val Val Val Asp Asn Ala Gly Leu Ala Leu Gly Thr Ala Pro
  1               5                  10                  15

Ala Pro Gln Val Pro Leu Lys Asp Trp Gln Thr Met Val Asn Thr Asn
                 20                  25                  30

Ile Thr Gly Leu Leu Asn Ile Thr His His Leu Leu Pro Thr Leu Ile
        35                  40                  45

Asp Arg Lys Gly Ile Val Val Asn Leu Ser Ser Val Ala Ala His Tyr
 50                  55                  60

Pro Tyr Thr Gly Gly Asn Val Tyr Cys Ala Ser Lys
 65                  70                  75

<210> SEQ ID NO 22
<211> LENGTH: 72
<212> TYPE: PRT
<213> ORGANISM: unknown
<220> FEATURE:
<223> OTHER INFORMATION: ZF0050310= Arthrobacter paraffineus

<400> SEQUENCE: 22

Gln Gly Ile Gly Tyr Ala Thr Ala Lys Arg Leu Ile Ser Leu Gly Ala
  1               5                  10                  15

Thr Val Ala Ile Gly Asp Ile Asp Glu Ala Thr Leu Ala Arg Ala Ala
                 20                  25                  30

Lys Asp Leu Gly Ile Arg Thr Phe Gly Arg Leu Asp Val Thr Asp Pro
        35                  40                  45

Ala Ser Phe Phe Asp Phe Leu Asp Thr Val Glu Gly Glu Leu Gly Pro
 50                  55                  60

Ile Asp Val Leu Ile Asn Asn Ala
 65                  70

<210> SEQ ID NO 23
<211> LENGTH: 75
<212> TYPE: PRT
<213> ORGANISM: unknown
<220> FEATURE:
<223> OTHER INFORMATION: ZF0050310= Arthrobacter paraffineus

<400> SEQUENCE: 23

Gln Arg Ile Gly Leu Glu Ile Ala Arg Thr Phe Ile Lys Glu Gly Ala
  1               5                  10                  15

Thr Val Val Leu Gly Asp Ile Asn Glu Thr Val Gly Thr Ala Ala Val
                 20                  25                  30

Ala Glu Leu Gly Gly Glu Ser Val Ala Arg Phe Ala Ser Cys Asp Val
        35                  40                  45
```

```
Arg Asp Ser Gly Gln Val Glu Ala Met Leu Asp Leu Ala Glu Ser Ala
    50                  55                  60

Phe Gly Pro Val Asp Val Met Met Asn Asn Ala
 65                  70                  75

<210> SEQ ID NO 24
<211> LENGTH: 72
<212> TYPE: PRT
<213> ORGANISM: unknown
<220> FEATURE:
<223> OTHER INFORMATION: ZF0050310= Arthrobacter paraffineus

<400> SEQUENCE: 24

Gln Gly Ile Gly Tyr Gln Thr Ala Lys Glu Leu Ile Arg Arg Gly His
  1               5                  10                  15

Arg Val Ala Ile Gly Asp Ile Asp Glu Ala Arg Ala Lys Glu Thr Ala
                 20                  25                  30

Ala Glu Leu Gly Val Lys Val Val Thr Arg Leu Asp Val Thr Asp Pro
            35                  40                  45

Asp Ser Phe Lys Asp Phe Leu Asp Leu Val Glu Gly Asp Leu Gly Pro
        50                  55                  60

Leu Asp Val Leu Ile Asn Asn Ala
 65                  70

<210> SEQ ID NO 25
<211> LENGTH: 74
<212> TYPE: PRT
<213> ORGANISM: unknown
<220> FEATURE:
<223> OTHER INFORMATION: ZF0050310= Arthrobacter paraffineus

<400> SEQUENCE: 25

Gly Ile Gly Leu Glu Ile Ala Arg Thr Phe Ile Lys Glu Gly Ala Thr
  1               5                  10                  15

Val Val Leu Gly Asp Ile Asn Glu Thr Val Gly Thr Ala Ala Val Ala
                 20                  25                  30

Glu Leu Gly Gly Glu Ser Val Ala Arg Phe Ala Ser Cys Asp Val Arg
            35                  40                  45

Asp Ser Gly Gln Val Glu Ala Met Leu Asp Leu Ala Glu Ser Ala Phe
        50                  55                  60

Gly Pro Val Asp Val Ile Val Asn Asn Ala
 65                  70

<210> SEQ ID NO 26
<211> LENGTH: 74
<212> TYPE: PRT
<213> ORGANISM: unknown
<220> FEATURE:
<223> OTHER INFORMATION: ZF0050310= Arthrobacter paraffineus

<400> SEQUENCE: 26

Ile Gly Leu Glu Ile Ala Arg Thr Phe Ile Lys Glu Gly Ala Thr Val
  1               5                  10                  15

Val Leu Gly Asp Ile Asn Glu Thr Val Gly Thr Ala Ala Val Gly Glu
                 20                  25                  30

Leu Gly Gly Glu Ser Val Ala Arg Phe Ala Ser Cys Asp Val Arg Asp
            35                  40                  45

Ser Gly Gln Val Glu Ala Met Leu Asp Leu Ala Glu Ser Ala Phe Gly
        50                  55                  60

Pro Val Asp Val Met Val Asn Asn Ala Gly
 65                  70
```

```
65                  70

<210> SEQ ID NO 27
<211> LENGTH: 62
<212> TYPE: PRT
<213> ORGANISM: unknown
<220> FEATURE:
<223> OTHER INFORMATION: ZF0002333= Rhodococcus erythropolis

<400> SEQUENCE: 27

Val Pro Val Ala Val Asp Leu His Ile Glu Ser Ala Lys Glu Thr
1               5                   10                  15

Val Ala Leu Ile Glu Ser Gln Tyr Gly Thr Pro Ala Leu Ala Leu Glu
                20                  25                  30

Ala Asp Val Arg Asp Arg Ala Ala Val Ser Ala Ala Phe Glu Ala Thr
            35                  40                  45

Val Ala Glu Trp Gly Arg Phe Asp Tyr Leu Val Asn Asn Ala
        50                  55                  60

<210> SEQ ID NO 28
<211> LENGTH: 74
<212> TYPE: PRT
<213> ORGANISM: unknown
<220> FEATURE:
<223> OTHER INFORMATION: ZF0002333= Rhodococcus erythropolis

<400> SEQUENCE: 28

Leu Gly Arg Glu Ile Ala Leu Lys Leu Ala Ser Glu Gly Ala Ser Val
1               5                   10                  15

Val Val Asn Asp Leu Asp Pro Glu Pro Ala Ala Gln Thr Glu Arg Asp
                20                  25                  30

Ile Lys Ala Thr Gly Gly Gln Ala Val Ser Cys Val Gly Ser Val Ala
            35                  40                  45

Glu Asp Gly Phe Ala Glu Arg Phe Val Asn Thr Ala Val Glu Ser Phe
        50                  55                  60

Gly Gly Leu Asp Val Met Val Asn Asn Ala
65                  70

<210> SEQ ID NO 29
<211> LENGTH: 76
<212> TYPE: PRT
<213> ORGANISM: unknown
<220> FEATURE:
<223> OTHER INFORMATION: ZF0002333= Rhodococcus erythropolis

<400> SEQUENCE: 29

Ala Gly Leu Gly Val Glu Phe Ala His Arg Phe Ala Ala Arg Gly Ala
1               5                   10                  15

Asn Leu Val Leu Val Ala Arg Arg Ala Asp Arg Leu Glu Ala Leu Ala
                20                  25                  30

Thr Glu Leu Arg Val Ala His Gly Ile Thr Val Thr Val Leu Pro Ala
            35                  40                  45

Asp Leu Ala Ala Pro Gly Val Gly Ala Thr Leu His Gln Glu Leu Thr
        50                  55                  60

Ser Arg Gly Ile Thr Val Thr Ser Leu Ile Asn Asn
65                  70                  75

<210> SEQ ID NO 30
<211> LENGTH: 72
<212> TYPE: PRT
<213> ORGANISM: unknown
```

```
<220> FEATURE:
<223> OTHER INFORMATION: ZF0003535= Actinomyces

<400> SEQUENCE: 30

Pro Ala Asp Gly Tyr Gln Thr Ala Lys Glu Leu Ile Arg Arg Gly His
1               5                   10                  15

Arg Val Ala Ile Val Asp Ile Asp Glu Ala Arg Ala Lys Gly Ala Ala
            20                  25                  30

Ala Glu Leu Gly Val Lys Val Thr Arg Leu Asp Val Thr Glu Pro
        35                  40                  45

Asp Ser Phe Thr Thr Phe Leu Asp Leu Val Arg Glu Leu Gly Pro
    50                  55                  60

Leu Asp Ile Leu Val Asn Asn Ala
65                  70

<210> SEQ ID NO 31
<211> LENGTH: 67
<212> TYPE: PRT
<213> ORGANISM: unknown
<220> FEATURE:
<223> OTHER INFORMATION: ZF0050310= Arthrobacter paraffineus

<400> SEQUENCE: 31

Ala Thr Asp Gly Ala Arg Val Ala Val Val Asp Leu His Ile Glu Ser
1               5                   10                  15

Ala Glu Glu Thr Val Ala Leu Ile Glu Ser Gln Tyr Gly Thr Pro Ala
            20                  25                  30

Leu Ala Leu Glu Ala Asp Val Arg Asp Arg Ala Ala Val Ser Ala Ala
        35                  40                  45

Phe Glu Ala Thr Val Ala Glu Trp Gly Arg Phe Asp Tyr Leu Val Asn
    50                  55                  60

Asn Ala Gly
65

<210> SEQ ID NO 32
<211> LENGTH: 67
<212> TYPE: PRT
<213> ORGANISM: unknown
<220> FEATURE:
<223> OTHER INFORMATION: ZF0050310= Arthrobacter paraffineus

<400> SEQUENCE: 32

Ala Ala Asp Gly Ala Arg Val Ala Val Val Asp Leu His Ile Glu Ser
1               5                   10                  15

Ala Lys Glu Thr Val Ala Leu Ile Glu Ser Gln Tyr Gly Thr Pro Ala
            20                  25                  30

Leu Ala Leu Glu Ala Asp Val Arg Asp Arg Ala Ala Val Ser Ala Ala
        35                  40                  45

Phe Glu Ala Thr Val Ala Glu Trp Gly Arg Phe Asp Tyr Leu Val Asn
    50                  55                  60

Asn Ala Gly
65

<210> SEQ ID NO 33
<211> LENGTH: 348
<212> TYPE: PRT
<213> ORGANISM: unknown
<220> FEATURE:
<223> OTHER INFORMATION: ZF0050310= Arthrobacter paraffineus

<400> SEQUENCE: 33
```

Met Lys Ala Ile Gln Tyr Ala Arg Ile Gly Ala Glu Pro Glu Leu Thr
1               5                   10                  15

Glu Ile Pro Lys Pro Glu Pro Gly Glu Val Leu Leu Glu Val
            20                  25                  30

Thr Ala Ala Gly Val Cys His Ser Asp Asp Phe Ile Met Ser Leu Pro
        35                  40                  45

Glu Glu Gln Tyr Thr Tyr Gly Leu Pro Leu Thr Leu Gly His Glu Gly
    50                  55                  60

Ala Gly Arg Val Ala Ala Val Gly Glu Gly Val Glu Gly Leu Asp Ile
65                  70                  75                  80

Gly Thr Asn Val Val Val Tyr Gly Pro Trp Gly Cys Gly Ser Cys Trp
                85                  90                  95

His Cys Ser Gln Gly Leu Glu Asn Tyr Cys Ser Arg Ala Lys Glu Leu
            100                 105                 110

Gly Ile Asn Pro Pro Gly Leu Gly Ala Pro Gly Ala Leu Ala Glu Phe
        115                 120                 125

Met Ile Val Asp Ser Pro Arg His Leu Val Pro Ile Gly Asp Leu Asp
130                 135                 140

Pro Val Lys Thr Val Pro Leu Thr Asp Ala Gly Leu Thr Pro Tyr His
145                 150                 155                 160

Ala Ile Lys Arg Ser Leu Pro Lys Leu Arg Gly Ala Tyr Ala Val
                165                 170                 175

Val Ile Gly Thr Gly Gly Leu Gly His Val Ala Ile Gln Leu Leu Arg
            180                 185                 190

His Leu Ser Ala Ala Thr Val Ile Ala Leu Asp Val Ser Ala Asp Lys
        195                 200                 205

Leu Glu Leu Ala Thr Lys Val Gly Ala His Glu Val Val Leu Ser Asp
210                 215                 220

Lys Asp Ala Ala Glu Asn Val Arg Arg Ile Thr Gly Ser Gln Gly Ala
225                 230                 235                 240

Ala Leu Val Leu Asp Phe Val Gly Tyr Gln Pro Thr Ile Asp Thr Ala
                245                 250                 255

Met Ala Val Ala Gly Val Gly Ser Asp Val Thr Ile Val Gly Ile Gly
            260                 265                 270

Asp Gly Gln Ala His Ala Lys Val Gly Phe Phe Gln Ser Pro Tyr Glu
        275                 280                 285

Ala Ser Val Thr Val Pro Tyr Trp Gly Ala Arg Asn Glu Leu Ile Glu
290                 295                 300

Leu Ile Asp Leu Ala His Ala Gly Ile Phe Asp Ile Ala Val Glu Thr
305                 310                 315                 320

Phe Ser Leu Asp Asn Gly Ala Glu Ala Tyr Arg Arg Leu Ala Ala Gly
                325                 330                 335

Thr Leu Ser Gly Arg Ala Val Val Pro Gly Leu
            340                 345

<210> SEQ ID NO 34
<211> LENGTH: 348
<212> TYPE: PRT
<213> ORGANISM: unknown
<220> FEATURE:
<223> OTHER INFORMATION: ZF0050310= Arthrobacter paraffineus

<400> SEQUENCE: 34

Met Lys Ala Ile Gln Tyr Thr Arg Ile Gly Ala Glu Pro Glu Leu Thr
1               5                   10                  15

```
Glu Ile Pro Lys Pro Glu Pro Gly Glu Val Leu Leu Glu Val
        20                  25                  30

Thr Ala Ala Gly Val Cys His Ser Asp Asp Phe Ile Met Ser Leu Pro
        35                  40                  45

Glu Glu Gln Tyr Thr Tyr Gly Leu Pro Leu Thr Leu Gly His Glu Gly
50                  55                  60

Ala Gly Arg Val Ala Ala Val Gly Glu Gly Val Glu Gly Leu Asp Ile
65                  70                  75                  80

Gly Thr Asn Val Val Tyr Gly Pro Trp Gly Cys Gly Ser Cys Trp
                85                  90                  95

His Cys Ser Gln Gly Leu Glu Asn Tyr Cys Ser Arg Ala Lys Glu Leu
                100                 105                 110

Gly Ile Asn Pro Pro Gly Leu Gly Ala Pro Gly Ala Leu Ala Glu Phe
                115                 120                 125

Met Ile Val Asp Ser Pro Arg His Leu Val Pro Ile Gly Asp Leu Asp
130                 135                 140

Pro Val Lys Thr Val Pro Leu Thr Asp Ala Gly Leu Thr Pro Tyr His
145                 150                 155                 160

Ala Ile Lys Arg Ser Leu Pro Lys Leu Arg Gly Gly Ala Tyr Ala Val
                165                 170                 175

Val Ile Gly Thr Gly Gly Leu Gly His Val Ala Ile Gln Leu Leu Arg
                180                 185                 190

His Leu Ser Ala Ala Thr Val Ile Ala Leu Asp Val Ser Ala Asp Lys
                195                 200                 205

Leu Glu Leu Ala Thr Lys Val Gly Ala His Glu Val Val Leu Ser Asp
210                 215                 220

Lys Asp Ala Ala Glu Asn Val Arg Arg Ile Thr Gly Ser Gln Gly Ala
225                 230                 235                 240

Ala Leu Val Leu Asp Phe Val Gly Tyr Gln Pro Thr Ile Asp Thr Ala
                245                 250                 255

Met Ala Val Ala Gly Val Gly Ser Asp Val Thr Ile Val Gly Ile Gly
                260                 265                 270

Asp Gly Gln Ala His Ala Lys Val Gly Phe Phe Gln Ser Pro Tyr Glu
                275                 280                 285

Ala Ser Val Thr Val Pro Tyr Trp Gly Ala Arg Asn Glu Leu Ile Glu
                290                 295                 300

Leu Ile Asp Leu Ala His Ala Gly Ile Phe Asp Ile Ala Val Glu Thr
305                 310                 315                 320

Phe Ser Leu Asp Asn Gly Ala Glu Ala Tyr Arg Arg Leu Ala Ala Gly
                325                 330                 335

Thr Leu Ser Gly Arg Ala Val Val Val Pro Gly Leu
                340                 345

<210> SEQ ID NO 35
<211> LENGTH: 488
<212> TYPE: DNA
<213> ORGANISM: unknown
<220> FEATURE:
<223> OTHER INFORMATION: ZF0002326= Actinoplanes missouriensis;
      ZF0003505= Streptomyces; ZF0050197= Pseudomonas oleovorans;
      ZF0050294= Rhodococcus; ZF0050330= Bacillus; ZF0051303= Bacterium;
      ZF0051337= Methylomonas; ZF0051321= Bacterium; ZF0050782=
      Lactobacillus bulgaricus;
<220> FEATURE:
<223> OTHER INFORMATION: ZF0050544= Phyllobacterium rubiacearum;
      ZF0002852= Rhodococcus; ZF0050310= Arthrobacter paraffineus;
      ZF0002862= Streptomyces clavuligerus; ZF0050292= Bacterium;
```

```
        ZF0002031= Streptomyces; ZF0002349= Streptomyces spectabilis;
        ZF0002434= Streptomyces;
<220> FEATURE:
<223> OTHER INFORMATION: ZF0002437= Streptomyces; ZF0003712=
        Micromonospora; ZF0003765= Streptomyces; ZF0051305= Bacterium;
        ZF0003513= Actinomyces; ZF0050993= Kocuria; ZF0002018=
        Streptomyces; ZF0003767= Actinomyces; ZF0002332= Streptomyces
        diastatochromogenes; ZF0003768= Actinomyces;
<220> FEATURE:
<223> OTHER INFORMATION: ZF0002379= Streptomyces coelescens; ZF0002351=
        Nonomuraea roseoviolacea; ZF0003769= Actinomyces;

<400> SEQUENCE: 35
gggccatggg gttgtggcaa ctgttggcac tgctcacaag gactcgagaa ctattgctct      60
cgcgcccaag aactcggaat caatcctccc ggtctcggtg cacccggcgc gttggccgag     120
ttcatgatcg tcgattctcc tcgccacctt gtcccgatcg gtgacctcga cccggtcaag     180
acggtgccgc tgaccgacgc cggtctgacg ccgtatcacg cgatcaagcg ttctctgccg     240
aaacttcgcg gaggctcgta cgcggttgtc attggtaccg gcgggctcgg ccacgtcgcc     300
attcagctcc tccgtcacct ctcggcgtca acggtcatcg ctttggacgt gagcgcggac     360
aagctcgaac tggcaaccaa ggtaggcgct cacgaagtgg ttctgtccga caaggacgcg     420
gccgagaacg tccgcaagat cactggaagt caaggcgccg cactggttct cgacttcgtt     480
ggctacca                                                              488

<210> SEQ ID NO 36
<211> LENGTH: 385
<212> TYPE: DNA
<213> ORGANISM: unknown
<220> FEATURE:
<223> OTHER INFORMATION: ZF0002326= Actinoplanes missouriensis;
        ZF0003505= Streptomyces; ZF0050197= Pseudomonas oleovorans;
        ZF0050294= Rhodococcus; ZF0050330= Bacillus; ZF0051303= Bacterium;
        ZF0051337= Methylomonas; ZF0051321= Bacterium; ZF0050782=
        Lactobacillus bulgaricus;
<220> FEATURE:
<223> OTHER INFORMATION: ZF0050544= Phyllobacterium rubiacearum;
        ZF0002852= Rhodococcus; ZF0050310= Arthrobacter paraffineus;
        ZF0002862= Streptomyces clavuligerus; ZF0050292= Bacterium;
        ZF0002031= Streptomyces; ZF0002349= Streptomyces spectabilis;
        ZF0002434= Streptomyces;
<220> FEATURE:
<223> OTHER INFORMATION: ZF0002437= Streptomyces; ZF0003712=
        Micromonospora; ZF0003765= Streptomyces; ZF0051305= Bacterium;
        ZF0003513= Actinomyces; ZF0050993= Kocuria; ZF0002018=
        Streptomyces; ZF0003767= Actinomyces; ZF0002332= Streptomyces
        diastatochromogenes; ZF0003768= Actinomyces; ZF0002379=
<220> FEATURE:
<223> OTHER INFORMATION: Streptomyces coelescens; ZF0002351= Nonomuraea
        roseoviolacea; ZF0003769= Actinomyces;

<400> SEQUENCE: 36
gggccatggg gttgtggcaa ctgttggcac tgctcacaag gactcgagaa ctattgctct      60
cgcgcccaag aactcggaat caatcctccc ggtctcggtg cacccggcgc gttggccgag     120
ttcatgatcg tcgattctcc tcgccacctt gtcccgatcg gtgacctcga cccggtcaag     180
acggtgccgc tgaccgacgc cggtctgacg ccgtatcacg cgatcaagcg ttctctgccg     240
aaacttcgcg gaggctcgta cgcggttgtc attggtaccg gcgggctcgg ccacgtcacc     300
attcagctcc tccgtcacct ctcggcggca acggtcatcg ctttggacgt gagcgcggac     360
aagctcgaac tggcaaccaa ggtag                                           385

<210> SEQ ID NO 37
<211> LENGTH: 486
<212> TYPE: DNA
```

<213> ORGANISM: unknown
<220> FEATURE:
<223> OTHER INFORMATION: ZF0050286= Corynebacterium hoagii

<400> SEQUENCE: 37

```
ggcccttggg gttgcggacg ttgctggcac tgcgcgcagg ggctcgagaa ctactgctcc      60
cgcgcaaggg aactcggcat cgccccaccc ggcttgggcg cgccgggcgc gatcgccgag     120
tacatgatcg tcgactcgcc gcgtcacctg gtcccgatcg gtgacctcga ccccgtcacg     180
acggtgccgc tgaccgacgc cgggctcacc ccgtaccacg cgatcaaacg gtcgctcggc     240
aagctccgcg ccggctcgta cgcagtcgtg atcggcaccg gaggcctcgg acacgtcggc     300
atccagctgc tccgccacct gtcccctgca cgcatcatcg ccctcgacgt caacgacgag     360
aagctcgcgt tcgcccgcga ggtcggcgcg cacgagaccg tgttgtcgaa cgccgacgcc     420
gccgcgaacg tccggaagat cacgggttcg gccggtgccg cgctggtcct agacttcgtc     480
ggctac                                                               486
```

<210> SEQ ID NO 38
<211> LENGTH: 483
<212> TYPE: DNA
<213> ORGANISM: unknown
<220> FEATURE:
<223> OTHER INFORMATION: ZF0050310= Arthrobacter paraffineus

<400> SEQUENCE: 38

```
ggcccatggg gctgtggcag ctgttggcac tgctcgcaag gactcgaaaa ctactgttct      60
cgggcaaaag aactcggcat caatcctcct ggtctcggtg caccggcgc gttggccgaa     120
ttcatgatcg tcgattcacc tcgccacctc gtcccgatcg gcgacctcga tccggtcaag     180
acggtgccac tgaccgacgc cggtctgact ccgtatcacg cgatcaagcg ttcactgccg     240
aaacttcgcg gtggcgcgta cgccgtcgtc atcggtaccg gcggtctcgg ccatgtcgcc     300
atccaactcc tccgccacct ctcggcagca accgtcatcg cactcgacgt gagcgcggac     360
aagctcgtac tggcaaccaa ggtaggcgct cacgaagtgg tcctgtccga caaggacgcg     420
gccgagaacg tccgcaggat caccggaagt cagggcgccg cactggttct tgacttcgtt     480
ggc                                                                  483
```

<210> SEQ ID NO 39
<211> LENGTH: 210
<212> TYPE: DNA
<213> ORGANISM: unknown
<220> FEATURE:
<223> OTHER INFORMATION: ZF0004210= Actinomyces; ZF0004212= Actinomyces;
    ZF0004211= Actinomyces; ZF0003860= Actinomyces; ZF0004218=
    Actinomyces; ZF0003868= Actinomadura; ZF0004213= Actinomyces;
    ZF0003876= Actinomyces; ZF0003866= Actinomyces; ZF0003864=
    Actinomyces;
<220> FEATURE:
<223> OTHER INFORMATION: ZF0003862= Actinomadura; ZF0003869=
    Actinomyces; ZF0003867= Actinomadura; ZF0004216= Actinomyces;
    ZF0004235= Actinomyces; ZF0004209= Actinomadura; ZF0004214=
    Actinomyces; ZF0003871= Actinomyces; ZF0004063= Actinomadura;
    ZF0004052= Actinomadura;
<220> FEATURE:
<223> OTHER INFORMATION: ZF0006405= Streptomyces; ZF0003865=
    Actinomadura; ZF0004047= Actinomadura; ZF0004070= Actinomyces;
    ZF0004085= Actinomyces; ZF0004217= Actinomyces; ZF0004089=
    Actinomadura; ZF0004090= Actinomadura; ZF0006138= Streptomyces;
    ZF0004236= Actinomadura;
<220> FEATURE:
<223> OTHER INFORMATION: ZF0051203= Bacterium;

<400> SEQUENCE: 39

```
ggaccgtggg gctgcggcac gtgcgtcaag tgcgccgagg gcaaggagaa ctactgcctg    60
cgcgccaagg aactcggcat cgccccgccc ggactcggct cgcccggcgc catggccgag   120
tacatgatcg tcgacgaccc gcgccacctg gtgccgctcg gcggtctcga cccggtccag   180
gccgtgccgc tcactgacgc gggcctgaca                                    210
```

<210> SEQ ID NO 40
<211> LENGTH: 282
<212> TYPE: DNA
<213> ORGANISM: unknown
<220> FEATURE:
<223> OTHER INFORMATION: ZF0002326= Actinoplanes missouriensis;
      ZF0003505= Streptomyces; ZF0051321= Bacterium; ZF0050782=
      Lactobacillus bulgaricus; ZF0050544= Phyllobacterium rubiacearum;
      ZF0002031= Streptomyces; ZF0002349= Streptomyces spectabilis;
      ZF0002434= Streptomyces; ZF0050993= Kocuria;
<220> FEATURE:
<223> OTHER INFORMATION: ZF0002018= Streptomyces; ZF0003767=
      Actinomyces; ZF0003764= Streptomyces; ZF0002331= Actinoplanes
      philippinensis; ZF0002441= Streptomyces; ZF0051307= Bacterium;
      ZF0051301= Bacterium; ZF0051240= Bacterium; ZF0002333= Rhodococcus
      erythropolis;
<220> FEATURE:
<223> OTHER INFORMATION: ZF0003713= Micromonospora; ZF0004980=
      Streptomyces; ZF0004821= Actinomyces; ZF0002359= Actinoplanes
      ianthinogenes; ZF0002396= Actinoplanes; ZF0003781= Actinomyces;
      ZF0003512= Actinomyces; ZF0006093= Streptomyces; ZF0006103=
      Streptomyces;
<220> FEATURE:
<223> OTHER INFORMATION: ZF0006087= Streptomyces; ZF0050446= Bacterium;
      ZF0050445= Bacterium; ZF0006086= Streptomyces; ZF0002322=
      Rhodococcus; ZF0003538= Actinomyces; ZF0003535= Actinomyces;

<400> SEQUENCE: 40

```
tgtcacaccg atcaccacat cgtcaccggc gcgaccccga tgccgtcgtt cccggtcatg    60
ggcgggcacg agggttcggg cgtcatcacc aagctcggcc ctgaggtcaa gggactggag   120
gtcggcgacc acgtcgttct gtccttcatt ccggcttgtg gaacctgtcc ggcgtgttcg   180
gccgggcatc agaatctttg tgacctcggg atgggcctcc tcagcggcca agccatcagc   240
gacggcacgt accggatcca ggctcgcggc gaaaacgtga tc                     282
```

<210> SEQ ID NO 41
<211> LENGTH: 276
<212> TYPE: DNA
<213> ORGANISM: unknown
<220> FEATURE:
<223> OTHER INFORMATION: ZF0002326= Actinoplanes missouriensis;
      ZF0003505= Streptomyces; ZF0051321= Bacterium; ZF0050782=
      Lactobacillus bulgaricus; ZF0050544= Phyllobacterium rubiacearum;
      ZF0002031= Streptomyces; ZF0002349= Streptomyces spectabilis;
      ZF0002434= Streptomyces; ZF0050993= Kocuria;
<220> FEATURE:
<223> OTHER INFORMATION: ZF0002018= Streptomyces; ZF0003767=
      Actinomyces; ZF0003764= Streptomyces; ZF0002331= Actinoplanes
      philippinensis; ZF0002441= Streptomyces; ZF0051307= Bacterium;
      ZF0051301= Bacterium; ZF0051240= Bacterium; ZF0002333= Rhodococcus
      erythropolis;
<220> FEATURE:
<223> OTHER INFORMATION: ZF0003713= Micromonospora; ZF0004980=
      Streptomyces; ZF0004821= Actinomyces; ZF0002359= Actinoplanes
      ianthinogenes; ZF0002396= Actinoplanes; ZF0003781= Actinomyces;
      ZF0003512= Actinomyces; ZF0006093= Streptomyces; ZF0006103=
      Streptomyces;
<220> FEATURE:
<223> OTHER INFORMATION: ZF0006087= Streptomyces; ZF0050446= Bacterium;
      ZF0050445= Bacterium; ZF0006086= Streptomyces; ZF0002322=
      Rhodococcus; ZF0003538= Actinomyces; ZF0003535= Actinomyces;

<400> SEQUENCE: 41

```
tgccataccg acgatcatgc tgtgaccggt gatctggcag tcccactccc cgtgatcggt      60
ggccacgaag gcgcgggcat agtggagaaa gtcggccccg gcgtgcgaga cgtcgaggta     120
ggcgatcacg tcgtcctctc cttcattccc tcgtgtggac gctgccgttg gtgcgcagtc     180
ggacagagca acctctgcga cctcggcgcc attctgatgg ccggcgcaca ggtcgacggg     240
acgtaccgcg cgacagctcg cgggcacgac gtcgga                               276
```

```
<210> SEQ ID NO 42
<211> LENGTH: 276
<212> TYPE: DNA
<213> ORGANISM: unknown
<220> FEATURE:
<223> OTHER INFORMATION: ZF0002326= Actinoplanes missouriensis;
      ZF0003505= Streptomyces; ZF0051321= Bacterium; ZF0050782=
      Lactobacillus bulgaricus; ZF0050544= Phyllobacterium rubiacearum;
      ZF0002031= Streptomyces; ZF0002349= Streptomyces spectabilis;
      ZF0002434= Streptomyces; ZF0050993= Kocuria;
<220> FEATURE:
<223> OTHER INFORMATION: ZF0002018= Streptomyces; ZF0003767=
      Actinomyces; ZF0003764= Streptomyces; ZF0002331= Actinoplanes
      philippinensis; ZF0002441= Streptomyces; ZF0051307= Bacterium;
      ZF0051301= Bacterium; ZF0051240= Bacterium; ZF0002333= Rhodococcus
      erythropolis;
<220> FEATURE:
<223> OTHER INFORMATION: ZF0003713= Micromonospora; ZF0004980=
      Streptomyces; ZF0004821= Actinomyces; ZF0002359= Actinoplanes
      ianthinogenes; ZF0002396= Actinoplanes; ZF0003781= Actinomyces;
      ZF0003512= Actinomyces; ZF0006093= Streptomyces; ZF0006103=
      Streptomyces;
<220> FEATURE:
<223> OTHER INFORMATION: ZF0006087= Streptomyces; ZF0050446= Bacterium;
      ZF0050445= Bacterium; ZF0006086= Streptomyces; ZF0002322=
      Rhodococcus; ZF0003538= Actinomyces; ZF0003535= Actinomyces;

<400> SEQUENCE: 42
```

```
tgccatacag acgatcatgc tgtgaccggt gatctggcag tcccactccc cgtgatcggt      60
ggccacgaag gcgcgggcat agtggagaaa gtcggccccg gcgtgcgaga cgtcgaggta     120
ggcgatcacg tcgtcctctc cttcattccc tcgtgtggac gctgccgttg gtgcgcagtc     180
ggacagagca acctctgcga cctcggcgcc attctgatgg ccggcgcaca ggtcgacggg     240
acgtaccgcg cgacagctcg cgggcacgac gtcgga                               276
```

```
<210> SEQ ID NO 43
<211> LENGTH: 276
<212> TYPE: DNA
<213> ORGANISM: unknown
<220> FEATURE:
<223> OTHER INFORMATION: ZF0002326= Actinoplanes missouriensis;
      ZF0003505= Streptomyces; ZF0051321= Bacterium; ZF0050782=
      Lactobacillus bulgaricus; ZF0050544= Phyllobacterium rubiacearum;
      ZF0002031= Streptomyces; ZF0002349= Streptomyces spectabilis;
      ZF0002434= Streptomyces; ZF0050993= Kocuria;
<220> FEATURE:
<223> OTHER INFORMATION: ZF0002018= Streptomyces; ZF0003767=
      Actinomyces; ZF0003764= Streptomyces; ZF0002331= Actinoplanes
      philippinensis; ZF0002441= Streptomyces; ZF0051307= Bacterium;
      ZF0051301= Bacterium; ZF0051240= Bacterium; ZF0002333= Rhodococcus
      erythropolis;
<220> FEATURE:
<223> OTHER INFORMATION: ZF0003713= Micromonospora; ZF0004980=
      Streptomyces; ZF0004821= Actinomyces; ZF0002359= Actinoplanes
      ianthinogenes; ZF0002396= Actinoplanes; ZF0003781= Actinomyces;
      ZF0003512= Actinomyces; ZF0006093= Streptomyces; ZF0006103=
      Streptomyces;
<220> FEATURE:
<223> OTHER INFORMATION: ZF0006087= Streptomyces; ZF0050446= Bacterium;
      ZF0050445= Bacterium; ZF0006086= Streptomyces; ZF0002322=
      Rhodococcus; ZF0003538= Actinomyces; ZF0003535= Actinomyces;

<400> SEQUENCE: 43
```

```
tgtcatactg acgatcatgc tgtgaccggt gatctggcag tcccactccc cgtgatcggt      60
ggccacgaag gcgcgggcat agtggagaaa gtcggccccg gcgtgcgaga cgtcgaggta     120
ggcgatcacg tcgtcctctc cttcattccc tcgtgtggac gctgccgttg gtgcgcagtc     180
ggacagagca acctctgcga cctcggcgcc attctgatgg ccggcgcaca ggtcgacggg     240
acgtaccgcg cgacagctcg cgggcacgac gtcgga                              276
```

<210> SEQ ID NO 44
<211> LENGTH: 276
<212> TYPE: DNA
<213> ORGANISM: unknown
<220> FEATURE:
<223> OTHER INFORMATION: ZF0002326= Actinoplanes missouriensis;
      ZF0003505= Streptomyces; ZF0051321= Bacterium; ZF0050782=
      Lactobacillus bulgaricus; ZF0050544= Phyllobacterium rubiacearum;
      ZF0002031= Streptomyces; ZF0002349= Streptomyces spectabilis;
      ZF0002434= Streptomyces; ZF0050993= Kocuria;
<220> FEATURE:
<223> OTHER INFORMATION: ZF0002018= Streptomyces; ZF0003767=
      Actinomyces; ZF0003764= Streptomyces; ZF0002331= Actinoplanes
      philippinensis; ZF0002441= Streptomyces; ZF0051307= Bacterium;
      ZF0051301= Bacterium; ZF0051240= Bacterium; ZF0002333= Rhodococcus
      erythropolis;
<220> FEATURE:
<223> OTHER INFORMATION: ZF0003713= Micromonospora; ZF0004980=
      Streptomyces; ZF0004821= Actinomyces; ZF0002359= Actinoplanes
      ianthinogenes; ZF0002396= Actinoplanes; ZF0003781= Actinomyces;
      ZF0003512= Actinomyces; ZF0006093= Streptomyces; ZF0006103=
      Streptomyces;
<220> FEATURE:
<223> OTHER INFORMATION: ZF0006087= Streptomyces; ZF0050446= Bacterium;
      ZF0050445= Bacterium; ZF0006086= Streptomyces; ZF0002322=
      Rhodococcus; ZF0003538= Actinomyces; ZF0003535= Actinomyces;

<400> SEQUENCE: 44

```
tgtcacaccg acgatcatgc tgtgaccggt gatctggcag tcccactccc cgtgatcggt      60
ggccacgaag gcgcgggcat agtggagaaa gtcggccccg gcgtgcgaga cgtcgaggta     120
ggcgatcacg tcgtcctctc cttcattccc tcgtgtggac gctgccgttg gtgcgcagtc     180
ggacagagca acctctgcga cctcggcgcc attctgatgg ccggcgcacg gtcgacggg      240 acgtaccgcg cgacagctcg cgggcacgac gtcgga                              276
```

<210> SEQ ID NO 45
<211> LENGTH: 276
<212> TYPE: DNA
<213> ORGANISM: unknown
<220> FEATURE:
<223> OTHER INFORMATION: ZF0002326= Actinoplanes missouriensis;
      ZF0003505= Streptomyces; ZF0051321= Bacterium; ZF0050782=
      Lactobacillus bulgaricus; ZF0050544= Phyllobacterium rubiacearum;
      ZF0002031= Streptomyces; ZF0002349= Streptomyces spectabilis;
      ZF0002434= Streptomyces; ZF0050993= Kocuria;
<220> FEATURE:
<223> OTHER INFORMATION: ZF0002018= Streptomyces; ZF0003767=
      Actinomyces; ZF0003764= Streptomyces; ZF0002331= Actinoplanes
      philippinensis; ZF0002441= Streptomyces; ZF0051307= Bacterium;
      ZF0051301= Bacterium; ZF0051240= Bacterium; ZF0002333= Rhodococcus
      erythropolis;
<220> FEATURE:
<223> OTHER INFORMATION: ZF0003713= Micromonospora; ZF0004980=
      Streptomyces; ZF0004821= Actinomyces; ZF0002359= Actinoplanes
      ianthinogenes; ZF0002396= Actinoplanes; ZF0003781= Actinomyces;
      ZF0003512= Actinomyces; ZF0006093= Streptomyces; ZF0006103=
      Streptomyces;
<220> FEATURE:
<223> OTHER INFORMATION: ZF0006087= Streptomyces; ZF0050446= Bacterium;
      ZF0050445= Bacterium; ZF0006086= Streptomyces; ZF0002322=
      Rhodococcus; ZF0003538= Actinomyces; ZF0003535= Actinomyces;

<400> SEQUENCE: 45

```
tgtcacactg acgatcatgc tgtgaccggt gatctggcag tcccactccc cgtgatcggt      60
ggccacgaag gcgcgggcat agtggagaaa gtcggccccg cgtgcgaga cgtcgaggta     120 ggcgatcacg tcgtcctctc cttcattccc tcgtgtggac gctgccgttg gtgcgcagtc    180
ggacagagca acctctgcga cctcggcgcc attctgatgg ccggcgcaca ggtcgacggg    240
acgtaccgcg cgacagctcg cgggcacgac gtcgga                              276
```

<210> SEQ ID NO 46
<211> LENGTH: 279
<212> TYPE: DNA
<213> ORGANISM: unknown
<220> FEATURE:
<223> OTHER INFORMATION: ZF0050310= Arthrobacter paraffineus

<400> SEQUENCE: 46

```
tgccacacag atctgttcac gaagtcggtg ctaccggaaa ggctcggccc ctgcgtgttc      60
gggcacgaag gagcgggggt ggtcgaggcc gtcggctcgt cgatcgacag cattgcgccc    120
ggtgatcacg tgttgctgag ctaccgcagt tgcggtgtgt gcaggcagtg cctcagcggt    180
catcgggcgt actgcgaaag ctcacacggg ctcaacagct ctggcgcacg caccgacggc    240
tcgacgccgg tccggcgaag cggaactccg atacggtcc                            279
```

<210> SEQ ID NO 47
<211> LENGTH: 279
<212> TYPE: DNA
<213> ORGANISM: unknown
<220> FEATURE:
<223> OTHER INFORMATION: ZF0002333= Rhodococcus erythropolis

<400> SEQUENCE: 47

```
tgtcatactg atctgttcac gaagacggtg ctaccggaaa agctcgggcc ctgcgtgttc      60
ggacacgaag gcgccggcgt cgtgcaagcc gttggctcgt cgatcgacaa catcgcggct    120
ggtgatcacg tattgctgag ctaccgcagt tgcggtgtat gcaggcaatg tctcagcgac    180
catcgggcgt actgcgaaag ctcacacggg ctcaacagct ctggcgcacg caccgacggc    240
tcgacgccgg tccggcgaaa cggaactccg atacggtcc                            279
```

<210> SEQ ID NO 48
<211> LENGTH: 360
<212> TYPE: DNA
<213> ORGANISM: unknown
<220> FEATURE:
<223> OTHER INFORMATION: ZF0051303= Bacterium; ZF0051337= Methylomonas;
      ZF0002862= Streptomyces clavuligerus; ZF0050292= Bacterium;
      ZF0051305= Bacterium; ZF0003513= Actinomyces; ZF0002351=
      Nonomuraea roseoviolacea; ZF0003769= Actinomyces; ZF0002017=
      Streptomyces; ZF0051306= Bacterium;
<220> FEATURE:
<223> OTHER INFORMATION: ZF0002016= Streptomyces; ZF0003504=
      Actinomyces; ZF0006073= Streptomyces; ZF0003770= Actinomyces;
      ZF0002352= Actinoplanes italicus; ZF0002378= Streptomyces
      aureomonopodiales; ZF0006089= Streptomyces; ZF0006106=
      Streptomyces; ZF0051325= Bacterium;
<220> FEATURE:
<223> OTHER INFORMATION: ZF0006108= Streptomyces; ZF0002440=
      Streptomyces; ZF0051302= Bacterium; ZF0003532= Actinomyces;
      ZF0003548= Nocardiaform;

<400> SEQUENCE: 48

```
tgcgggacgg accgcgagat cgcctcgggc atctacgggt gggcgccgcc gggacgcgaa      60
cacctcgtcc tcgggcacga atcgctgggc cgagtacgca ccgcgcccga cggcagcggt    120
```

```
ttcgccgccg gtgatctcgt cgtcgggatc gtgcgcaggc ccgatccggt gccgtgcggg      180
gcgtgtgcgc acggtgagtt cgacatgtgc cgcaacggtg agtacgtcga gcgcgggatc      240
aagcagatcg acgggtacgg gtcgacgtcg tgggtggtgg acgccgacta cacggtcaag      300
ctggacccgg cgctcaccga ggtgggtgtg ctgatggaac cgacgacggt gcttggccaa      360
```

<210> SEQ ID NO 49
<211> LENGTH: 421
<212> TYPE: DNA
<213> ORGANISM: unknown
<220> FEATURE:
<223> OTHER INFORMATION: ZF0051303= Bacterium; ZF0051337= Methylomonas;
      ZF0002862= Streptomyces clavuligerus; ZF0050292= Bacterium;
      ZF0051305= Bacterium; ZF0003513= Actinomyces; ZF0002351=
      Nonomuraea roseoviolacea; ZF0003769= Actinomyces; ZF0002017=
      Streptomyces; ZF0051306= Bacterium;
<220> FEATURE:
<223> OTHER INFORMATION: ZF0002016= Streptomyces; ZF0003504=
      Actinomyces; ZF0006073= Streptomyces; ZF0003770= Actinomyces;
      ZF0002352= Actinoplanes italicus; ZF0002378= Streptomyces
      aureomonopodiales; ZF0006089= Streptomyces; ZF0006106=
      Streptomyces; ZF0051325= Bacterium;
<220> FEATURE:
<223> OTHER INFORMATION: ZF0006108= Streptomyces; ZF0002440=
      Streptomyces; ZF0051302= Bacterium; ZF0003532= Actinomyces;
      ZF0003548= Nocardiaform;

<400> SEQUENCE: 49

```
tgtggtaccg acctgcacat ccggtcctgg acggatgggc gcagaagac catcgccacc       60 ccgctcacgc tcgccacga gttcgtcggc gaggtcgtcg agaccggccg cgacgtgacc      120
gacatccagg tcggcgacct ggtcagcggc gagggccacc tggtctgcgg caagtgccgc      180
aactgcctgg ccgccgccg tcacctgtgc cgcgcgaccg tcggcctcgg tgtcggccgt      240
gacggcgcct tcgccgagta cgtggtgctg cccgcctcca acgtgtgggt gcaccgggtg      300
ccggtcgacc tcgacgtcgc cgcgatcttc gacccgttcg gcaacgcggt gcacaccgcg      360
ctctccttcc cgctcgtcgg cgaggacgtg ctggtcaccg gtgccggtac catcggcatc      420
t                                                                    421
```

<210> SEQ ID NO 50
<211> LENGTH: 414
<212> TYPE: DNA
<213> ORGANISM: unknown
<220> FEATURE:
<223> OTHER INFORMATION: ZF0050197= Pseudomonas oleovorans; ZF0050294=
      Rhodococcus; ZF0050330= Bacillus, ZF0002852= Rhodococcus;
      ZF0050310= Arthrobacter paraffineus; ZF0002437= Streptomyces;
      ZF0003712= Micromonospora; ZF0003765= Streptomyces; ZF0002332=
      Streptomyces diatsatochromogenes;
<220> FEATURE:
<223> OTHER INFORMATION: ZF0003768= Actinomyces; ZF0002379= Streptomyces
      coelescens; ZF0002443= Streptomyces; ZF0002442= Streptomyces;
      ZF0002436= Streptomyces; ZF0050994= Bacterium; ZF0050992=
      Bacterium; ZF0050442= Bacterium; ZF0002049= Streptomyces;
      ZF0006069= Streptomyces;
<220> FEATURE:
<223> OTHER INFORMATION: ZF0006075= Streptomyces; ZF0004724=
      Nocardiaform; ZF0002392= Actinoplanes nipponensis; ZF0002356=
      Actinoplanes brasiliensis; ZF0003501= Actinomyces; ZF0051322=
      Bacterium; ZF0006078= Streptomyces; ZF0006092= Streptomyces;
      ZF0006090= Streptomyces;
<220> FEATURE:
<223> OTHER INFORMATION: ZF0006084= Streptomyces; ZF0006068=
      Streptomyces; ZF0050284= Rhodococcus; ZF0050028= Agrobacterium
      tumefaciens; ZF0003540= Actinomyces; ZF0003528= Actinomyces;
      ZF0003529= Actinomyces;

<400> SEQUENCE: 50

```
ggcctgacga tcggccatga accggtgggc gtcatcgaaa agctgggcag cgccgtgacg      60
ggttaccgcg agggccaacg cgtgatcgcc ggcgcgatct gccccaactt caattcgtat     120
gccgcgcagg atggcgcgcc gtcgcaggat ggcagctacc tggtggccag cggcgcatgc     180
ggctgccatg gataccgggc cacggccggc tggcgctttg caacatcat cgatggcgcc      240 caggccgaat acctgctggt tcccgatgcg cagggcaatc tggcgccggt tccggacaac     300
ctgagcgatg aacaggtgct gatgtgcccg acatcatgt ccaccggctt caaaggcgca      360
gagaacgcac acatccgcat cggcgacacg gtggcggtat ttgcgcaggg acca           414
```

<210> SEQ ID NO 51
<211> LENGTH: 432
<212> TYPE: DNA
<213> ORGANISM: unknown
<220> FEATURE:
<223> OTHER INFORMATION: ZF0050197= Pseudomonas oleovorans; ZF0050294=
      Rhodococcus; ZF0050330= Bacillus, ZF0002852= Rhodococcus;
      ZF0050310= Arthrobacter paraffineus; ZF0002437= Streptomyces;
      ZF0003712= Micromonospora; ZF0003765= Streptomyces; ZF0002332=
      Streptomyces diatsatochromogenes;
<220> FEATURE:
<223> OTHER INFORMATION: ZF0003768= Actinomyces; ZF0002379= Streptomyces
      coelescens; ZF0002443= Streptomyces; ZF0002442= Streptomyces;
      ZF0002436= Streptomyces; ZF0050994= Bacterium; ZF0050992=
      Bacterium; ZF0050442= Bacterium; ZF0002049= Streptomyces;
      ZF0006069= Streptomyces;
<220> FEATURE:
<223> OTHER INFORMATION: ZF0006075= Streptomyces; ZF0004724=
      Nocardiaform; ZF0002392= Actinoplanes nipponensis; ZF0002356=
      Actinoplanes brasiliensis; ZF0003501= Actinomyces; ZF0051322=
      Bacterium; ZF0006078= Streptomyces; ZF0006092= Streptomyces;
      ZF0006090= Streptomyces;
<220> FEATURE:
<223> OTHER INFORMATION: ZF0006084= Streptomyces; ZF0006068=
      Streptomyces; ZF0050284= Rhodococcus; ZF0050028= Agrobacterium
      tumefaciens; ZF0003540= Actinomyces; ZF0003528= Actinomyces;
      ZF0003529= Actinomyces;

<400> SEQUENCE: 51

```
tgcgggacgg acctgcacat cctcggaggt gacgtccccg aggtgaccga cgggcgaatc      60
ctgggccacg aggccgtcgg gaccgtggtc gaggtgggcg acggcgtaca gacactcgcg     120
ccgggcgatc gcgtgctcgt tcgtgtgtc accgcatgcg gtacgtgccg gttctgccgc      180
gagagccgct acgggcaatg cctcggaggc ggcggctgga tcctcggaca cctgatcgac     240
ggcacccagg ccgaactcgt ccagttccg tacgccgaca attcgaccca ccgcatcccc      300
gacggtgtga gcgacgagca gatgctcatg ctcgccgaca tcctgcccac ctcctacgag     360
gtcggtgttc tcaacggctg tctccggccg gcggacgtcg tcgtcatcat cggggccgac     420
gatcggcctc tt                                                          432
```

<210> SEQ ID NO 52
<211> LENGTH: 220
<212> TYPE: DNA
<213> ORGANISM: unknown
<220> FEATURE:
<223> OTHER INFORMATION: ZF0050310= Arthrobacter paraffineus

<400> SEQUENCE: 52

```
cgtcgacgtc gtcgtcgaca acgcgggatt cggaacacac ggggcattcg tggacgaaga      60
tcacgagcgc gtcacgtccg agattcagct caacatcgcc acgctggtcg agctgacaca     120
cacattcccg cccgaccttc tcaccggccg cggagcactg gtcaacatcg ccagcacagc     180
gtcgttccag ccgacaccgg gcatggccgt ctactgcgct                            220
```

<210> SEQ ID NO 53
<211> LENGTH: 226
<212> TYPE: DNA
<213> ORGANISM: unknown
<220> FEATURE:
<223> OTHER INFORMATION: ZF0050310= Arthrobacter paraffineus

<400> SEQUENCE: 53
cgtcgacgtc gtcgtccaca acgccggatt cggaacacac ggggcattcg tggacgaaga      60
tctcgagcgc gtcacgtccg agattcagct caacatcgcc acgctggtcg agctgacaca     120
cacattcctg cccgaccttc tcaccggccg cggagcactg gtcaacatcg ccagcacagc     180
gtcgttccag ccgacaccgg gcatggccgt ctactgcgcc accaag                    226

<210> SEQ ID NO 54
<211> LENGTH: 237
<212> TYPE: DNA
<213> ORGANISM: unknown
<220> FEATURE:
<223> OTHER INFORMATION: ZF0003535= Actinomyces

<400> SEQUENCE: 54
cgtgtcgacg tcgtggtgca caatgctgcg atcactcaaa aggccacttt tcgcgacatt      60 accccgccg attttgagcg catcctgcgg gtgaacctga ccggcgtctt caacctgagc     120
caagccgtca ttcccttgat gattcagcgc ggcggaggaa gcatcgtctc gatttcctcg     180
ctgtcggcgc agaacggcgg ggggatcttc ggcggcgccc actattgcgc aaccaag       237

<210> SEQ ID NO 55
<211> LENGTH: 229
<212> TYPE: DNA
<213> ORGANISM: unknown
<220> FEATURE:
<223> OTHER INFORMATION: ZF0003535= Actinomyces

<400> SEQUENCE: 55
cgtcgacgtc gtcgtcgaca acgccggtct ggcactgggc acggccccg cgccgcaggt      60 gccgctaaag gactggcaga ccatggtgaa caccaacatc accggtctac tgaacatcac     120
ccaccatctc ctgccgacac tgatcgaccg taaaggtatc gtcgtcaacc tttcgtctgt     180
tgccgcgcac tatccctata cgggcggcaa tgtatactgc gcctccaag                229

<210> SEQ ID NO 56
<211> LENGTH: 216
<212> TYPE: DNA
<213> ORGANISM: unknown
<220> FEATURE:
<223> OTHER INFORMATION: ZF0050310= Arthrobacter paraffineus

<400> SEQUENCE: 56 cagggatcg gatacgccac cgcgaagcgg ctgatcagcc tgggtgcgac ggtcgcgatc      60
ggcgacatcg acgaagccac tctcgcgcga gcagccaagg atttgggcat ccgcacgttc     120
gggcgcctcg acgtcaccga ccccgcctcg ttcttcgact tcctcgacac cgtcgaaggt     180
gaactcggcc cgatcgacgt gctgatcaac aacgcg                              216

<210> SEQ ID NO 57
<211> LENGTH: 225
<212> TYPE: DNA
<213> ORGANISM: unknown
<220> FEATURE:

<223> OTHER INFORMATION: ZF0080310= Arthrobacter paraffineus

<400> SEQUENCE: 57

```
cagcggatcg ggctcgaaat tgcgcgcacc ttcatcaagg aaggcgcgac cgtcgttctc    60
ggcgacatca acgaaaccgt gggaacggct gcggtcgccg aactcggtgg agagtcggtc   120
gcccgtttcg cttcctgcga cgtgcgtgac tccggacagg tcgaggccat gctcgatctg   180
gccgaaagcg ctttcggtcc agtcgatgtc atgatgaaca acgcg                   225
```

<210> SEQ ID NO 58
<211> LENGTH: 216
<212> TYPE: DNA
<213> ORGANISM: unknown
<220> FEATURE:
<223> OTHER INFORMATION: ZF0080310= Arthrobacter paraffineus

<400> SEQUENCE: 58

```
caggggatcg gctaccagac cgcgaaggag ctgatccgac gaggtcaccg cgtggccatc    60
ggcgacatcg acgaggcacg tgctaaggag accgccgccg aactgggggt taaggttgtc   120
acccgcctcg atgtcaccga ccctgactcg ttcaaagact ttctcgacct agtcgaggga   180
gacctcggcc ccctcgacgt gctgatcaac aacgcg                             216
```

<210> SEQ ID NO 59
<211> LENGTH: 222
<212> TYPE: DNA
<213> ORGANISM: unknown
<220> FEATURE:
<223> OTHER INFORMATION: ZF0080310= Arthrobacter paraffineus

<400> SEQUENCE: 59

```
gggatcgggc tcgaaattgc gcgcaccttc atcaaggaag gcgcgaccgt cgttctcggc    60
gacatcaacg aaaccgtggg aacggctgcg gtcgccgaac tcggtggaga gtcggtcgcc   120
cgtttcgctt cctgcgacgt gcgtgactcc ggacaggtcg aggccatgct cgatctggcc   180
gaaagcgctt tcggtccagt cgatgtcatc gtgaacaacg cg                      222
```

<210> SEQ ID NO 60
<211> LENGTH: 222
<212> TYPE: DNA
<213> ORGANISM: unknown
<220> FEATURE:
<223> OTHER INFORMATION: ZF0080310= Arthrobacter paraffineus

<400> SEQUENCE: 60

```
atcgggctcg aaattgcgcg caccttcatc aaggaaggcg cgaccgtcgt tctcggcgac    60
atcaacgaaa ccgtgggaac ggctgcggtc ggcgaactcg gtggagagtc ggtcgcccgt   120
ttcgcttcct gcgacgtgcg tgactccgga caggtcgagg ccatgctcga tctggccgaa   180
agcgctttcg gtccagtcga tgtcatggtc aacaacgccg gc                      222
```

<210> SEQ ID NO 61
<211> LENGTH: 186
<212> TYPE: DNA
<213> ORGANISM: unknown
<220> FEATURE:
<223> OTHER INFORMATION: ZF0002333= Rhodococcus erythropolis

<400> SEQUENCE: 61

```
gtgccggtcg cggtcgtgga ccttcacatc gaaagtgcaa aggagaccgt cgacttatc     60
gaatcgcagt acggcacacc cgcgctcgcc cttgaggccg atgtgcgcga ccgcgccgcc   120
```

```
gtgagcgccg ctttcgaagc caccgtcgcc gaatggggac gcttcgacta cctcgtcaac      180
aacgcc                                                                 186

<210> SEQ ID NO 62
<211> LENGTH: 222
<212> TYPE: DNA
<213> ORGANISM: unknown
<220> FEATURE:
<223> OTHER INFORMATION: ZF0002333= Rhodococcus erythropolis

<400> SEQUENCE: 62
ctcggccgtg aaatcgctct caagctcgct tccgaaggcg cctcggtagt ggtcaacgac      60
ctcgatcccg aacctgccgc tcagaccgag cgcgatatca aagccacagg tggacaggct     120
gtctcgtgcg tcggctccgt tgccgaggac gggttcgccg aacgcttcgt gaacactgcc     180
gtcgaatcat tcggcggact cgacgtcatg gtgaacaacg cg                        222

<210> SEQ ID NO 63
<211> LENGTH: 231
<212> TYPE: DNA
<213> ORGANISM: unknown
<220> FEATURE:
<223> OTHER INFORMATION: ZF0002333= Rhodococcus erythropolis

<400> SEQUENCE: 63
gcggggctcg gagtggaatt cgctcaccgc ttcgccgctc gcggtgcaaa tctggttctc      60
gtcgccaggc gggcagatcg cctcgaagcc ctcgctaccg aactccgcgt cgcccacggc     120
atcacagtca cagttctgcc tgccgacctg gcggcgcccg gcgtcggcgc aacactgcac     180
caggagctga caagccgtgg catcaccgtc acctcgctga tcaacaacgc c              231

<210> SEQ ID NO 64
<211> LENGTH: 216
<212> TYPE: DNA
<213> ORGANISM: unknown
<220> FEATURE:
<223> OTHER INFORMATION: ZF0003535= Actinomyces

<400> SEQUENCE: 64
ccagcggacg gctatcagac agcgaaggag ttgattcgac gaggccaccg ggtcgccatc      60
gtcgacatcg acgaggcacg tgcgaagggg gccgccgccg aactcggggt gaaggtcgtc     120
acccgactcg acgtcaccga acctgactcg ttcacaacgt ttctggacct ggtcgaacgt     180
gaactcggac ccctcgacat cctggtcaac aacgcg                               216

<210> SEQ ID NO 65
<211> LENGTH: 201
<212> TYPE: DNA
<213> ORGANISM: unknown
<220> FEATURE:
<223> OTHER INFORMATION: ZF0050310= Arthrobacter paraffineus

<400> SEQUENCE: 65
gccacggacg gtgcccgcgt cgcggtcgtg gaccttcaca tcgaaagtgc agaggagacc      60
gtcgcactta tcgaatcgca gtacggcaca cccgcgctcg cccttgaggc cgatgtgcgc     120
gaccgcgccg ccgtgagcgc cgctttcgaa gccaccgtcg ccgaatgggg acgcttcgac     180
tacctcgtca caacgccgg c                                                201

<210> SEQ ID NO 66
```

<211> LENGTH: 201
<212> TYPE: DNA
<213> ORGANISM: unknown
<220> FEATURE:
<223> OTHER INFORMATION: ZF0050310= Arthrobacter paraffineus

<400> SEQUENCE: 66

| | |
|---|---|
| gccgcggacg gtgcccgcgt cgcggtcgtg gaccttcaca tcgaaagtgc aaaggagacc | 60 |
| gtcgcactta tcgaatcgca gtacggcaca cccgcgctcg cccttgaggc cgatgtgcgc | 120 |
| gaccgcgccg ccgtgagcgc cgctttcgaa gccaccgtcg ccgaatgggg acgcttcgac | 180 |
| tacctcgtca acaacgccgg c | 201 |

<210> SEQ ID NO 67
<211> LENGTH: 1047
<212> TYPE: DNA
<213> ORGANISM: unknown
<220> FEATURE:
<223> OTHER INFORMATION: ZF0050310= Arthrobacter paraffineus

<400> SEQUENCE: 67

| | |
|---|---|
| atgaaggcaa tccagtacgc gagaatcggc gcagaacccg aactcacgga gattcccaaa | 60 |
| cccgagcccg gtccaggtga agtgctcctg gaagtcaccg ctgccggcgt ctgccactcg | 120 |
| gacgacttca tcatgagcct gcccgaagag cagtacacct acggccttcc tctcacgctc | 180 |
| ggccacgaag gcgccggccg ggtcgccgcc gtcggcgagg gcgtcgaagg actcgacatc | 240 |
| ggaaccaatg tcgtcgtcta cggacccctgg ggctgtggca gctgttggca ctgctcgcaa | 300 |
| ggactcgaaa actactgttc tcgggcaaaa gaactcggca tcaatcctcc tggtctcggt | 360 |
| gcacccggcg cgttggccga attcatgatc gtcgattcac ctcgccacct cgtcccgatc | 420 |
| ggcgacctcg atccggtcaa gacggtgcca ctgaccgacg ccggtctgac tccgtatcac | 480 |
| gcgatcaagc gttcactgcc gaaacttcgc ggtggcgcgt acgccgtcgt catcggtacc | 540 |
| ggcggtctcg gccatgtcgc catccaactc ctccgccacc tctcggcagc aaccgtcatc | 600 |
| gcactcgacg tgagcgcgga caagctcgaa ctggcaacca aggtaggcgc tcacgaagtg | 660 |
| gtcctgtccg acaaggacgc ggccgagaac gtccgcagga tcaccggaag tcagggcgcc | 720 |
| gcactggttc tcgacttcgt cggctatcag cccaccatcg acaccgcgat ggctgtcgcc | 780 |
| ggcgtcggat cggacgtcac gatcgtcggg atcggcgacg ggcaggccca tgccaaagtc | 840 |
| gggttcttcc aaagtcctta cgaggcttct gtgacagttc cgtactgggg tgcccgcaac | 900 |
| gagctgatcg aattgatcga cctggcgcac gccggcatct tcgacatcgc ggtggagacc | 960 |
| ttcagtctcg acaacggcgc cgaagcgtat cgacgactgg ccgccggaac gctcagcggc | 1020 |
| cgcgcggttg tggtccctgg tctgtag | 1047 |

<210> SEQ ID NO 68
<211> LENGTH: 1047
<212> TYPE: DNA
<213> ORGANISM: unknown
<220> FEATURE:
<223> OTHER INFORMATION: ZF0050310= Arthrobacter paraffineus

<400> SEQUENCE: 68

| | |
|---|---|
| atgaaggcaa tccagtacac gagaatcggc gcagaacccg aactcacgga gattcccaaa | 60 |
| cccgagcccg gtccaggtga agtgctcctg gaagtcaccg ctgccggcgt ctgccactcg | 120 |
| gacgacttca tcatgagcct gcccgaagag cagtacacct acggccttcc tctcacgctc | 180 |
| ggccacgaag gcgccggccg ggtcgccgcc gtcggcgagg gcgtcgaagg actcgacatc | 240 |

```
ggaaccaatg tcgtcgtcta cggaccctgg ggctgtggca gctgttggca ctgctcgcaa    300
ggactcgaaa actactgttc tcgggcaaaa gaactcggca tcaatcctcc tggtctcggt    360
gcacccggcg cgttggccga attcatgatc gtcgattcac ctcgccacct cgtcccgatc    420
ggcgacctcg atccggtcaa gacggtgcca ctgaccgacg ccggtctgac tccgtatcac    480
gcgatcaagc gttcactgcc gaaacttcgc ggtggcgcgt acgccgtcgt catcggtacc    540
ggcggtctcg gccatgtcgc catccaactc ctccgccacc tctcggcagc aaccgtcatc    600
gcactcgacg tgagcgcgga caagctcgaa ctggcaacca aggtaggcgc tcacgaagtg    660
gtcctgtccg acaaggacgc ggccgagaac gtccgcagga tcaccggaag tcagggcgcc    720
gcactggttc tcgacttcgt cggctatcag cccaccatcg acaccgcgat ggctgtcgcc    780
ggcgtcggat cggacgtcac gatcgtcggg atcggcgacg ggcaggccca tgccaaagtc    840
gggttcttcc aaagtcctta cgaggcttct gtgacagttc cgtactgggg tgcccgcaac    900
gagctgatcg aattgatcga cctggcgcac gccggcatct tcgacatcgc ggtggagacc    960
ttcagtctcg acaacggcgc cgaagcgtat cgacgactgg ccgccggaac gctcagcggc   1020
cgcgcggttg tggtccctgg tctgtag                                       1047
```